US012746215B2

(12) United States Patent
Agvald et al.

(10) Patent No.: US 12,746,215 B2
(45) **Date of Patent: *Sep. 29, 2026**

(54) MONO- AND BIS-NITROSYLATED PROPANEDIOLS FOR THERAPEUTIC USE

(71) Applicant: ATTGENO AB, Solna (SE)

(72) Inventors: Per Håkan Agvald, Stockholm (SE); Kristofer Bo Ingemar Nilsson, Örebro (SE); Leif Christofer Adding, Åkersberga (SE); Anna Karolina Maria Stene Hurtsén, Karlstad (SE)

(73) Assignee: ATTGENO BIO, Solna (SE)

( * ) Notice: Subject to any disclaimer, the term of this patent is extended or adjusted under 35 U.S.C. 154(b) by 757 days.

This patent is subject to a terminal disclaimer.

(21) Appl. No.: 17/927,774

(22) PCT Filed: May 27, 2021

(86) PCT No.: PCT/EP2021/064234

§ 371 (c)(1),
(2) Date: Nov. 25, 2022

(87) PCT Pub. No.: WO2021/239892

PCT Pub. Date: Dec. 2, 2021

(65) Prior Publication Data

US 2023/0201132 A1 Jun. 29, 2023

(30) Foreign Application Priority Data

May 27, 2020 (GB) ..................................... 2007929

(51) Int. Cl.

| | |
|---|---|
| ***A61K 31/045*** | (2006.01) |
| ***A61M 11/04*** | (2006.01) |
| ***A61M 15/06*** | (2006.01) |
| ***A61P 9/12*** | (2006.01) |

(52) U.S. Cl.

CPC .............. *A61K 31/045* (2013.01); *A61P 9/12* (2018.01); *A61M 11/042* (2014.02); *A61M 15/06* (2013.01)

(58) Field of Classification Search

CPC ....... A61K 31/04; A61K 31/045; A61P 15/10; A61P 9/10; A61P 9/00; A61P 11/06

See application file for complete search history.

(56) References Cited

U.S. PATENT DOCUMENTS

| | | | | |
|---|---|---|---|---|
| 5,278,192 | A | 1/1994 | Fung et al. | |
| 5,646,181 | A | 7/1997 | Fung et al. | |
| 5,670,177 | A | 9/1997 | Briend et al. | |
| 6,103,769 | A | 8/2000 | Kelm | |
| 12,486,216 | B2 * | 12/2025 | Agvald ..................... | A61P 9/12 |
| 2009/0298141 | A1 | 12/2009 | De Vries et al. | |
| 2014/0271731 | A1 | 9/2014 | Perricone | |

FOREIGN PATENT DOCUMENTS

| | | |
|---|---|---|
| WO | WO 93/05709 | 4/1993 |
| WO | WO 94/01103 | 1/1994 |
| WO | WO 94/16740 | 8/1994 |
| WO | WO 95/02181 | 1/1995 |
| WO | WO 02/068334 | 9/2002 |
| WO | WO 2006/031191 | 3/2006 |
| WO | WO 2007/106034 | 9/2007 |
| WO | WO 2020/109420 | 6/2020 |

OTHER PUBLICATIONS

Kuhn et al., J. Am. Chem. Soc. 1954, 76(2), pp. 328-329.
Barrington et al., Cochrane Database Syst. Rev., 2001, 4, CD000399.
Cederqvist et al., Biochem. Pharmacol., 1994, 47, 1047-53.
Chotigeat et al., J. Med. Assoc. Thai., 2007, 90, 266-71.
Gustafsson et al., Biochem. Biophys. Res. Commun., 1991, 181, 852-7.
Hurtsen, A.S. et al., Drug Design Development and Therapy, 2020, 14, 635-645.
Hui-li, Cardiovascular Therapeutics, 29, 2011, 153-175.
Larsen et al., N. Eng. J. Med, 2006, 355, 2792-3.
Nilsson, K. F. et al., Biochem Pharmacol., 82(3), 248-259 (2011).
Persson et al., Acta Physiol. Scand., 1990, 140, 449-57.
Rosenkranz, Stephan et al., European Heart Journal, 37(12), 942-954 (2016).
Simonneau, Gerald et al., European Respiratory Journal, 53(1), PMID:30545968 (2019).
Summerfield et al., Respir. Care., 2011, 57, 444-8.
Tiller, D et al., PLoS One, 8(3), e59225 (2013).
International Search Report and Written Opinion were mailed on Aug. 12, 2021 by the International Searching Authority for International Application No. PCT/EP2021/064234 filed on May 27, 2021 and published as WO 2021/239892 (Applicant—Attgeno AB) (11 pages).
Nilsson, et al. The novel nitric oxide donor PDNO attenuates ovine ischemia-reperfusion induced renal failure, Intensive Care Medicine Experimental, 5, 1, 2017.
V.S. Shagov, Spectrophotometric method for determination of 1,4-butylene glycol, Journal of Analytical Chemistry, 1966, vol. XXI, Issue 1, pp. 122-125.

* cited by examiner

*Primary Examiner* — Kevin E Weddington
(74) *Attorney, Agent, or Firm* — Ballard Spahr LLP

(57) ABSTRACT

The present invention relates to methods of treating a condition wherein NO has a beneficial effect, wherein such treatment comprises administering certain mono- and/or bis nitrosylated propanediols, including compositions and formulations thereof, wherein administration of said compounds, compositions or formulations is indirect to the pulmonary circulation and/or the systemic circulation of a patient in need thereof.

15 Claims, 13 Drawing Sheets

MONO- AND BIS-NITROSYLATED PROPANEDIOLS FOR THERAPEUTIC USE

FIELD OF INVENTION

The present invention relates to methods of treating a condition wherein NO has a beneficial effect, wherein such treatment comprises administering certain mono- and/or bis-nitrosylated propanediols, including compositions and formulations thereof, wherein administration of said compounds, compositions or formulations is indirect to the pulmonary circulation and/or the systemic circulation of a patient in need thereof.

BACKGROUND OF THE INVENTION

The listing or discussion of an apparently prior-published document in this specification should not necessarily be taken as an acknowledgment that the document is part of the state of the art or common general knowledge.

Pulmonary hypertension (PH) was, until recently, defined as an increase in mean pulmonary arterial pressure (mPAP) at or above 25 mmHg at rest and it can be divided in more slowly developing chronic forms (cPH) and acute pulmonary hypertension (aPH) (which also may be referred to as acute developed hypertension). This definition was recently updated to refer to an increase in mean pulmonary arterial pressure (mPAP) at or above 20 mmHg at rest in combination with a pulmonary vascular resistance ≥3 Wood Units in all forms of pre-capillary pulmonary hypertension (Simonneau, Gérald et al., *European Respiratory Journal,* 53(1), PMID:30545968 (2019)). In aPH, acute induced constriction of the pulmonary vessels rapidly increases mPAP; it could be elicited as a response to a variety conditions such as major surgery (e.g. heart surgery), lung emboli, adult respiratory distress syndrome and sepsis. In aPH in otherwise healthy people no adaption of the right heart has been developed, which increases the risk for right heart failure. Furthermore, the patients are typically severely ill from the condition eliciting the aPH and normally have critically low systemic blood pressure, although low systemic blood pressure is not always present in all patients. In patients with the more chronic forms of PH, aPH could superposed on the chronic PH leading to deleterious high pressure resulting in right heart failure and even death. aPH is a vast problem causing untimely death and suffering to millions of people in the world and, given that diagnosis usually demands right heart catheterization and efficient lung-selective treatments are lacking, the full extent of the problem is not well understood.

Under normal conditions the right heart receives deoxygenated blood from the systemic circulation and pumps the blood through the lungs, where the cardiac output of the pulmonary circulation equals the volume of the blood circulating all other body organs. Despite the high flow rate through the lungs, blood pressure in the pulmonary circulation is only one fifth of that in the systemic circulation. The low resistance in the pulmonary circulation is attributed to large cross-sectional area of pulmonary arteries and the fact that pulmonary vessels are much shorter than the systemic vessels. The left heart is a strong pump (working against a high pressure) that makes blood flow in the systemic circulation to e.g. the brain, liver, stomach, kidneys and the heart itself, and it is common knowledge that high blood pressure in the systemic circulation can cause many health problems including heart failure, stroke and kidney disease.

Many physiological factors influence the complex control of the blood flow in the systemic and pulmonary circulation. The blood vessels in the systemic circulation are normally in a state of vasoconstriction (small muscles in the vessel wall are continuously activated by the sympathetic nervous system to contract the vessel) whereas blood vessels in the pulmonary circulation are under constant vasodilation (i.e. relaxed, widened vessels in response to the continuous influence of oxygen and endogenously produced nitric oxide) thereby maintaining the very low resistance to blood flow and a resulting very low blood pressure compared to the systemic circulation.

In a variety of life-threatening diseases and after major surgeries the pathophysiological response leads to an intense inflammatory reaction, which in turn alters the physiologic state of systemic and pulmonary blood vessels. These alterations commonly result in a condition where the systemic blood vessels suddenly dilate and a critically low systemic blood pressure (systemic hypotension) develops, which may diminish the blood flow to the vital organs such as the brain, heart, liver and kidney. In parallel, and paradoxically, the pulmonary blood vessels abruptly constrict, in part due to reduced pulmonary nitric oxide production, leading to aPH and right heart failure, which reduces the cardiac output and further aggravates the systemic hypotension. These critically ill and hemodynamically unstable patients normally have to be treated in intensive care units, where the challenging mission is to balance drug therapies using vasopressor and heart strengthening drugs to restore the systemic blood pressure and pulmonary vasodilating drugs to attenuate the acute life-threatening pulmonary hypertension.

aPH is frequently underdiagnosed and treatment is often delayed (Rosenkranz, Stephan et al., *European Heart Journal,* 37(12), 942-954 (2016)). The reason for aPH being so fatal is that the right heart is a weak pump normally working against a low pressure and risks failing (right heart failure) if the mean pressure in the pulmonary circulation rapidly reaches >40 mmHg. Acute PH is a distinct critical condition and should not be confused with chronic pulmonary hypertension (Tiller, D et al., PLoS One, 8(3), e59225 (2013), Hui-li, Cardiovascular Therapeutics, 29, 2011, 153-175). In chronic diseases, when pressure in the pulmonary circulation over time gradually increases the right heart will adapt and increase in size and strength, and much higher outflow pressures can then be sustained. Even people in good health who, for example, contract an infection, a pulmonary embolus (blood clot in the lung) or undergo major surgery can develop aPH with deteriorating complications.

To overcome the systemic side effects of i.v. administered vasodilator drugs, administration by inhalation of nitric oxide or prostacyclin has been developed. Unfortunately, these drugs, even if effective in some cases, are often insufficient because they reach only parts of the lung that are ventilated.

Nitric oxide (NO) is a molecule of importance in several biological systems. It is continuously produced in the lung and can be measured at ppb (parts per billion) levels in expired gas. The discovery of endogenous NO in exhaled air, and its use as a diagnostic marker of inflammation, dates to the early 1990s (see, for example, WO 93/05709 and WO 95/02181). Today, the significance of endogenous NO is widely recognised, as evidenced by the commercial availability of a clinical NO analyser (NIOX®, the first tailor-made NO analyser for routine clinical use in asthma patients, which was originally manufactured by AEROCRINE AB, Solna, Sweden).

Since these early experiments, it has become generally recognised that endogenous nitric oxide (NO) is of critical importance as a mediator of vasodilation in blood vessels. In particular, nitric oxide plays an important role in the modulation of pulmonary vascular tone to optimise ventilation-perfusion matching in healthy human adults (i.e. matching the air that reaches the alveoli with the blood that reaches the alveoli via the capillaries, so that the oxygen provided via ventilation is just sufficient to fully saturate the blood; see, for example, Persson et al., *Acta Physiol. Scand.,* 1990, 140, 449-57). Measuring NO in exhaled breath is a good way of monitoring changes in endogenous NO production or scavenging in the lung (Gustafsson et al., *Biochem. Biophys. Res. Commun.,* 1991, 181, 852-7).

Since ventilation-perfusion matching disturbances and increased pulmonary artery blood pressure are features of pulmonary embolism, NO has been tested as a potential treatment. For example, U.S. Pat. No. 5,670,177 describes a method for treating or preventing ischemia comprising administering to a patient by an intravascular route a gaseous mixture comprising NO and carbon dioxide wherein the NO is present in an amount effective to treat or prevent ischemia. U.S. Pat. No. 6,103,769 discloses a similar method, with the difference that a NO-saturated saline solution is used.

Furthermore, nitric oxide/oxygen blends are used as a last-resort gas mixture in critical care to promote capillary and pulmonary dilation to treat primary pulmonary hypertension in neonatal patients and post-meconium aspiration related to birth defects (see Barrington et al., *Cochrane Database Syst. Rev.,* 2001, 4, CD000399 and Chotigeat et al., *J. Med. Assoc. Thai.,* 2007, 90, 266-71). Similarly, NO is administered as salvage therapy in patients with acute right ventricular failure secondary to pulmonary embolism (Summerfield et al., *Respir. Care.,* 2011, 57, 444-8). Inhaled NO is also approved in Europe, Australia and Japan for the treatment of aPH in cardiac surgery patients.

As an alternative to providing NO as a gas or dissolved in solution, others have investigated the use of NO-delivering compounds. For example, WO 94/16740 describes the use of NO-delivering compounds, such as S-nitrosothiols, thionitrites, thionitrates, sydnonimines, furoxans, organic nitrates, nitroprusside, nitroglycerin, iron-nitrosyl compounds, etc, for the treatment or prevention of alcoholic liver injury.

Nitrates are presently used to treat the symptoms of angina (chest pain). Nitrates work by relaxing blood vessels and increasing the supply of blood and oxygen to the heart while reducing its workload. Examples of presently available nitrate drugs include:

a) Nitroglycerin (glyceryl trinitrate) (1,2,3-propantriol-nitrate), which is today mostly taken sublingually to curb an acute attack of angina. However, strong headaches and dizziness due to the rapid and general vasodilatory effect are frequently encountered side-effects. Nitroglycerin infusion concentrates are also available and are diluted in isotonic glucose or physiological saline for intravenous infusion. Tolerance development (i.e. diminished efficacy with repeated or continuous dosage) is a clinical problem with Nitroglycerine (and other organic nitrates) treatment.

b) Isosorbide mononitrate (1,4:3,6-dianhydro-D-glucitol-5-nitrate), which is taken as prophylactic against angina pectoris. Tolerance development is a problem in long-term treatment regimens. Frequent side-effects include headache and dizziness, as encountered with nitroglycerin.

c) Isosorbide dinitrate (1,4:3,6-dianhydro-D-glucitol-2,5-nitrate), which is taken both acutely and prophylactically against angina pectoris and cardiac insufficiency.

d) Pentaerythrityl nitrates, a group of organic nitrates, which are known to exert long-term antioxidant and anti-atherogenic effects by currently unidentified mechanisms. Pentaerythrityl tetranitrate has been investigated in the context of nitrate tolerance, an unwanted development in nitrate therapy, and experimentally tested in pulmonary hypertension.

A number of these nitrate compounds, as well as other nitrate and nitrite compounds, have been tested in vivo and found to generate NO. For example, glyceryl trinitrate, ethyl nitrite, isobutyl nitrate, isobutyl nitrite, isoamyl nitrite and butyl nitrite have been tested in a rabbit model and were found to give a significant correlation between the in vivo generation of NO and effects on blood pressure (Cederqvist et al., *Biochem. Pharmacol.,* 1994, 47, 1047-53).

Accordingly, it has been suggested that certain organic nitrites have utility in treating male impotence and erectile dysfunction through topical or intracavernosal administration to the penis (see U.S. Pat. No. 5,646,181).

With the growing knowledge regarding the importance of nitric oxide also the importance of dietary composition has been recognised since it could influence the availability of NO in the arginine-nitric oxide system and its role in host defence has been discovered (Larsen et al., *N. Eng. J. Med,* 2006, 355, 2792-3). Hence, L-arginine, and esters thereof, such as the ethyl-, methyl- and butyl-L-arginine have been used to increase the endogenous production of NO.

WO 2006/031191 describes compositions and methods for use in the therapeutic delivery of gaseous nitric oxide. Such compositions for the delivery of the gaseous NO comprise a compound capable of forming a reversible bond or association to NO, such as alcohols, carbohydrates and proteins.

WO 2007/106034 describes methods for producing organic nitrites from a compound which is a mono/polyhydric alcohol, or an aldehyde- or ketone-derivate thereof. The methods involve the de-aeration of an aqueous solution of said compound, followed by purging with gaseous nitric oxide (NO).

Nilsson, K. F. et al., *Biochem Pharmacol.,* 82(3), 248-259 (2011) discusses the formation and identification of new bioactive organic nitrites.

Despite recent advances, there are a number of disadvantages associated with the use of currently known compounds for the treatment of conditions wherein administration of NO has a beneficial effect.

For example, among the compounds and compositions presently available, many are associated with undesired properties or side-effects, such as toxicity problems, delayed action, irreversible action or prolonged action, etc. One particular problem, frequently encountered when administering a NO-donating compound in the form of an infusion or inhalation is the production of methemoglobin (metHb).

A major therapeutic limitation inherent to organic nitrates, the most commonly used NO-donating drugs, is the development of tolerance, which occurs during chronic treatment with these agents.

Another problem associated with administrating NO-donating compounds in the form of an infusion, particularly when administrating the compounds intravenously and intraarterially, is that a professional is needed to perform the administration. This normally requires that the patient in need of the treatment is required to be in hospital care to receive it. Accordingly, valuable time could be lost as the aPH progresses and the requirement for hospital care severely affects the daily life of the patient if they suffer from chronic PH. Furthermore, if infusions have to be maintained over long periods of time this also increases the risk of infections in the patients. Further risks with peripheral infusions are thrombophlebitis and infusion on the side of the vessel causing tissue oedema with pain and inflammation. Central infusion catheters can cause intrathoracic bleeding, infection and pneumothorax.

Furthermore, known organic nitrites and their therapeutic use are frequently associated with problems likely to be due to impurities and degradation products present in the compositions. It is also difficult to prepare pharmaceutical formulations containing organic nitrites, as the mixing steps and vehicles used may trigger further degradation, and limits the maximal dose (concentration) of inhaled nitric oxide that can be continuously administered.

Additionally, using inhaled nitric oxide and oxygen has significant problems due to the production of nitrogen dioxide, which must be monitored continuously during administration.

Some preparation methods of the prior art provide only a relatively low concentration of organic nitrite in aqueous solution, meaning that the storage and transportation properties of such formulations are often less than satisfactory.

In addition, the preparation methods of the prior art result in significant quantities of NO gas and inorganic nitrite dissolved in solution, in addition to the desired organic nitrite. Due to the highly reactive properties of NO, it is necessary to handle and store the solution carefully in order to avoid sudden and spontaneous decomposition. It is also likely that NO gas reacts with plastic materials in the storage container or infusion aggregates, tubings and catheters. Moreover, the presence of inorganic nitrites increases the metHb fraction of the blood, which is a dose-limiting side effect.

There exists, therefore, a significant and urgent need for new treatments for conditions wherein NO has a beneficial effect which overcome one or more of the disadvantages identified above in the prior art. There also exists a need for improved routes for administering such compositions.

DESCRIPTION OF THE INVENTION

The present inventors have unexpectedly found that administration of mono- and/or bis-nitrosylated propanediols indirectly to the pulmonary circulation and/or the systemic circulation of a patient has biological effects that can treat conditions wherein NO has a beneficial effect.

Unless otherwise indicated, all technical and scientific terms used herein have the same meaning as commonly understood by one of ordinary skill in the art to which this invention pertains.

All embodiments of the invention and particular features mentioned herein may be taken in isolation or in combination with any other embodiments and/or particular features mentioned herein (hence describing more particular embodiments and particular features as disclosed herein) without departing from the disclosure of the invention.

As used herein, the term "comprises" will take its usual meaning in the art, namely indicating that the component includes but is not limited to the relevant features (i.e. including, among other things). As such, the term "comprises" will include references to the component consisting essentially of the relevant substance(s).

As used herein, unless otherwise specified the terms "consists essentially of" and "consisting essentially of" will refer to the relevant component being formed of at least 80% (e.g. at least 85%, at least 90%, or at least 95%, such as at least 99%) of the specified substance(s), according to the relevant measure (e.g. by weight thereof). The terms "consists essentially of" and "consisting essentially of" may be replaced with "consists of" and "consisting of", respectively.

For the avoidance of doubt, the term "comprises" will also include references to the component "consisting essentially of" (and in particular "consisting of") the relevant substance(s).

As outlined above, all embodiments of the invention and particular features mentioned herein may be taken in isolation or in combination with any other embodiments and/or particular features mentioned herein (hence describing more particular embodiments and particular features as disclosed herein) without departing from the disclosure of the invention.

In particular, any embodiments of the medical uses may be combined with the embodiments of the non-aqueous composition. Furthermore, any of the embodiments of the devices may be combined with any of the embodiments of the medical uses and/or non-aqueous composition.

Medical Uses

According to a first aspect of the invention, there is provided a compound of formula (I):

(I)

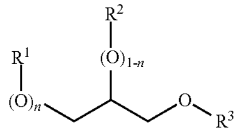

wherein $R^1$, $R^2$ and $R^3$ each independently represent H or —NO, wherein n is 0 or 1;

wherein when n is 0, $R^1$ is H; and wherein when n is 1, $R^2$ is H, provided that at least one of $R^1$ $R^2$ and $R^3$ represents —NO, for use in the treatment of a condition wherein NO has a beneficial effect, wherein the compound of formula (I) is administered indirectly to the pulmonary circulation and/or the systemic circulation of a patient.

According to a second aspect of the invention there is provided a substantially non-aqueous composition comprising:

(a) one or more compounds of formula (I):

(I)

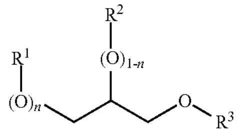

wherein $R^1$, $R^2$ and $R^3$ each independently represent H or —NO, wherein n is 0 or 1; and wherein when n is 0, $R^1$ is H and wherein when n is 1, $R^2$ is H, provided that at least one of $R^1$ $R^2$ and $R^3$ represents —NO and (b) a compound of formula I but wherein $R^1$, $R^2$ and $R^3$ represent H, For use in the treatment of a condition wherein NO has a beneficial effect, wherein the compound of formula (I) is administered indirectly to the pulmonary circulation and/or the systemic circulation of a patient.

As an alternative embodiment for the first aspect of the invention, there is provided a method of treating a condition wherein NO has a beneficial effect comprising administering to a patient in need thereof a therapeutically effective amount of a compound of formula (I) indirectly to the pulmonary circulation and/or the systemic circulation of the patient:

(I)

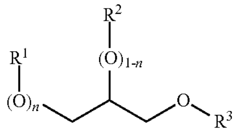

wherein $R^1$, $R^2$ and $R^3$ each independently represent H or —NO, wherein n is 0 or 1;

wherein when n is 0, $R^1$ is H; and wherein when n is 1, $R^2$ is H, provided that at least one of $R^1$ $R^2$ and $R^3$ represents —NO.

As an alternative embodiment of the second aspect of the invention there is provided a method of treating a condition wherein NO has a beneficial effect comprising administering to a patient in need thereof a therapeutically effective amount of a substantially non-aqueous composition indirectly to the pulmonary circulation and/or the systemic circulation of the patient, wherein the substantially non-aqueous composition comprises:

(a) one or more compounds of formula (I):

(I)

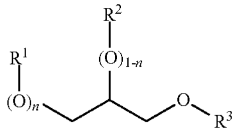

wherein $R^1$, $R^2$ and $R^3$ each independently represent H or —NO, wherein n is 0 or 1; and wherein when n is 0, $R^1$ is H and wherein when n is 1, $R^2$ is H, provided that at least one of $R^1$ $R^2$ and $R^3$ represents —NO and (b) a compound of formula I but wherein $R^1$, $R^2$ and $R^3$ represent H, As an alternative embodiment of the first aspect of the invention, there is also provided the use of a compound according to formula (I):

(I)

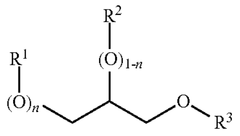

wherein $R^1$, $R^2$ and $R^3$ each independently represent H or —NO, wherein n is 0 or 1;

wherein when n is 0, $R^1$ is H; and wherein when n is 1, $R^2$ is H, provided that at least one of $R^1$ $R^2$ and $R^3$ represents —NO, for the manufacture of a medicament for a method of treatment of a condition wherein NO has a beneficial effect, wherein the compound of formula (I) is administered indirectly to the pulmonary circulation and/or the systemic circulation of a patient.

When administering the compound of formula (I) intravenously or intraarterially (i.e. directly to the patient, for example directly into the blood of the patient), the compound needs to be combined with a suitable aqueous buffer, otherwise it can cause damage to blood cells via hemolysis due to osmotic stress. The inventors have surprisingly found that the administration can be simplified as the aqueous buffer is not needed when the compound is administered indirectly to the blood circulation of a patient.

Although it is envisaged that osmosis is the most likely mechanism of hemolysis when administering the compound of formula (I) intravenously or intraarterially (i.e. directly to the patient), other mechanisms of hemolysis may also be occurring.

Furthermore, indirect administration methods can be carried out by the patients themselves without the requirement for a medical professional to perform the administration, or for a medical professional to perform preparatory steps for the patient to self-administer, such as implanting venous catheters so a patient can inject directly into their circulatory system. Therefore, these administrative routes simplify the administration process, reduce overall costs and lead to more effective treatment of the condition. Furthermore, indirect administration methods also reduce the risk of side-effects caused by invasive administration.

As used herein, the term "pulmonary circulation" refers to the portion of the circulatory system which carries deoxygenated blood away from the right ventricle, to the lungs, and returns oxygenated blood to the left atrium and ventricle of the heart. The vessels of the pulmonary circulation are the pulmonary arteries, pulmonary arterioles, pulmonary metarterioles, pulmonary capillaries, pulmonary venules and the pulmonary veins.

As used herein, the term "systemic circulation" refers to the portion of the cardiovascular system which transports oxygenated blood away from the heart through the aorta from the left ventricle where the blood has been previously deposited from pulmonary circulation, to the rest of the body, and returns oxygen-depleted blood back to the heart.

The skilled person will understand that references to the treatment of a particular condition (or, similarly, to treating that condition) take their normal meanings in the field of medicine. In particular, the terms may refer to achieving a reduction in the severity of one or more clinical symptoms and/or signs associated with the condition. For example, in the case of pulmonary embolism, the term may refer to achieving reduction in the severity of chest pain, shortness of breath and/or pulmonary hypertension via vasodilation. Furthermore, in the case of pulmonary embolism, the term may also refer to achieving pulmonary vasodilation or a decrease in pulmonary vascular resistance and right ventricular strain.

It will be understood that although in the context of the invention the compound of formula (I) is administered indirectly to the pulmonary circulation and/or the systemic circulation of a patient, it may also cause a direct effect on the particular organ or region at which the compound of formula (I) is applied.

As used herein, references to patients will refer to a living subject being treated, including mammalian (e.g. human) patients. In particular, the term patient may refer to a human subject. The term patient may also refer to animals (e.g. mammals), such as household pets (e.g. cats and, in particular, dogs), livestock and horses.

As used herein, the term "effective amount" will refer to an amount of a compound that confers a therapeutic effect on the treated patient. The effect may be objective (i.e. measurable by some test or marker) or subjective (i.e. the subject gives an indication of and/or feels an effect).

As indicated herein, the compounds and compositions of the invention are useful in the treatment of a condition wherein NO, i.e. administration of NO, has a beneficial effect.

As used herein, the term "beneficial effect" means that the use/administration of the compounds/compositions of the invention leads to an identifiable treatment, and/or improvement, of the condition in the patient being treated. The beneficial effect may be temporary or permanent and may be measured or determined by a medical practitioner or by the patient themselves. The beneficial effect may be experienced locally, e.g. just in one organ of the patient, or it may be experienced over the whole body of the patient depending on the route of administration and the condition being treated. The beneficial effect may be objective (i.e. measurable by some test or marker) or subjective (i.e. the subject gives an indication of and/or feels an effect).

Particular conditions that may be mentioned include those selected from the group consisting of: acute pulmonary vasoconstriction of different genesis; pulmonary hypertension of different genesis, including primary hypertension and secondary hypertension; preclampsia; eclampsia; conditions of different genesis in need of vasodilation; erectile dysfunction, systemic hypertension of different genesis; regional vasoconstriction of different genesis; local vasoconstriction of different genesis; acute heart failure (with or without preserved ejection fraction (HFpEF)); coronary heart disease; myocardial infarction; ischemic heart disease; angina pectoris; instable angina; cardiac arrhythmia; acute pulmonary hypertension in cardiac surgery patients; acidosis; inflammation of the airways; cystic fibrosis; COPD; immotile cilia syndrome; inflammation of the lung; pulmonary fibrosis; acute lung injury (ALI); adult respiratory distress syndrome; acute pulmonary oedema; acute mountain sickness; asthma; bronchitis; hypoxia of different genesis; ischemic disease of different genesis; stroke; cerebral vasoconstriction; inflammation of the gastrointestinal tract; gastrointestinal dysfunction; gastrointestinal complication; IBD; Crohn's disease; ulcerous colitis; liver disease; pancreas disease; inflammation of the bladder of the urethral tract; inflammation of the urinary bladder and ureters of the urethral tract; inflammation of the skin; diabetic ulcers; diabetic neuropathy; psoriasis; inflammation of different genesis; wound healing; organ protection in ischemia-reperfusion conditions; organ transplantation; tissue transplantation; cell transplantation; acute kidney disease; uterus relaxation; cervix relaxation; conditions where smooth muscle relaxation is needed; and disease of the eye, such as glaucoma.

More particular conditions that may be mentioned are all conditions of chronic or acute pulmonary hypertension. The pulmonary hypertension could be primary hypertension, or secondary hypertension and resulting in acute heart failure (with or without preserved ejection fraction (HFpEF)). For example, the condition may be pulmonary hypertension resulting from surgery.

Pulmonary hypertension is defined as an increase in mean pulmonary arterial pressure (mPAP) at or above 20 mmHg at rest in combination with a Wood Units value of >3 (Simonneau, Gérald et al., *European Respiratory Journal,* 53(1), PMID:30545968 (2019)).

The skilled person will be able to determine a suitable dose of active ingredients to be used in treatment based on the nature of the formulation used, the administration route, the condition to be treated and the status (e.g. state of illness) of the patient. For example, when administered indirectly to the pulmonary circulation of a human adult a suitable dose may result in the level of the compounds according to formula (I) in the pulmonary circulation of the patient of about 0.5 to about 3,000 nmol/kg/min, such as about 1 to about 3,000 nmol/kg/min, for example from about 5 to about 3,000 nmol/kg/min of the compound(s) of formula I. Such doses may be administered indirectly to the pulmonary circulation (either continuous or pulsed), such as over an extended period of time (e.g. 1 to 2 hours or even up to one, two or three weeks), or may be administered as a single (bolus) dose (such as a one-off dose or a single dose per treatment intervention, such as a single dose as required, or a single dose in each 24 hour period during treatment).

However, the skilled person will understand that in some circumstances the does may be higher than outlined above. For example, when administered subcutaneously for example, the injection results in a depot which slowly releases the compounds according to Formula (I) to the blood stream. The depot may be a larger dose than outlined above that can be released for a long time. This also applies to intramuscular, dermal and gastrointestinal routes of administration.

In an embodiment, where the administration is by subcutaneous injection (e.g. subcutaneous administration), the dose of the compound of formula (I) is in the range of from about 1 to about 30,000 nmol $kg^{-1}$ $min^{-1}$, such as from about 100 to about 2000 nmol $kg^{-1}$ $min^{-1}$.

In an embodiment, where the administration is by intramuscular injection (e.g. intramuscular administration), the dose of the compound of formula (I) is in the range of from about 1 to about 30,000 nmol $kg^{-1}$ $min^{-1}$, such as from about 10 to about 1000 nmol $kg^{-1}$ $min^{-1}$.

In an embodiment, where the administration is intranasal, the dose of the compound of formula (I) is in the range of from about 1 to about 30,000 nmol $kg^{-1}$, such as from about 100 to about 3000 nmol $kg^{-1}$.

In an embodiment, where the administration is sublingual, the dose of the compound of formula (I) is in the range of from about 1 to about 30,000 nmol $kg^{-1}$, such as from about 100 to about 3000 nmol $kg^{-1}$.

In an embodiment, where the administration is dermal, the dose of the compound of formula (I) is in the range of from about 1 to about 50,000 nmol $kg^{-1}$, for example from about 50 to about 30,000 nmol $kg^{-1}$ such as from about 100 to about 3000 nmol $kg^{-1}$.

The skilled person will understand that the temperature at which compounds of formula (I) are administered in treatment (i.e. administered to a subject) may be that of the environment in which administration takes place (i.e. room temperature) or may be controlled.

For example, such formulations administered intranasally, subcutaneously or intramuscularly at room temperature or at a reduced temperature (i.e. a temperature that is below room temperature), such as from about −10° C. to about 25° C., such as from about −5° C. to about 25° C., for example from about 0 to about 25° C.

The administration may be via inhalation, such as inhalation of a vapour comprising the compound of formula (I), or a nebulised composition comprising the compound of formula (I).

When administered by nebulisation/atomisation (e.g., in the form of a vapour or droplet spray) the formulations may be heated for administration by inhalation.

Without wishing to be bound by theory, it is believed that upon administration to a patient, the compounds of formula I are hydrolysed to release nitric oxide, which provides the desired therapeutic effect. In particular, it is surprising that the administration of the compound of formula (I) by other routes than intravenous or intraarterial could have any effect.

Specifically, it would previously have been believed by those skilled in the art that administration of a compound of formula (I) indirectly to the pulmonary circulation and/or systemic circulation of a patient, would result in the transnitrosylation and/or hydrolysis of the compound due to its chemically unstable nature. That is to say, that the transnitrosylation or hydrolysis (i.e. breakdown) of the compound of formula (I) would occur in the local tissue or region that it is administered in and would not reach the pulmonary circulation and/or systemic circulation.

For example, when administering the compound indirectly to the pulmonary circulation and/or systemic circulation of a patient, more time is required until the compound reaches the target organ compared to intravenous or intraarterial administration. Therefore, it has previously been believed that the compound would be inactivated before reaching the desired location in the body, when administered indirectly.

However, the inventors have found that sufficient amounts of the compound of formula (I) remain active after being administered indirectly to the pulmonary circulation and/or systemic circulation of a patient, whereby it may be transported to various organs at which the compounds may provide a biological effect.

For the avoidance of doubt, to administer a compound indirectly to the pulmonary circulation and/or systemic circulation of a patient refers to administering it by other means than direct injection to the pulmonary or systemic circulation.

The administration route may be to an epithelial layer (e.g. a mucus membrane or the skin) of a patient, e.g. via inhalation or intranasally, or the administration may be carried out subcutaneously or intramuscularly.

The term "epithelial layer" refers to the skin, the membranes of the reproductive, respiratory, urinary and digestive tracts, and the surfaces of the organs of a patient.

More specifically, it refers to the epithelial tissues that line the outer surfaces of organs and blood vessels through the body, as well as the inner surfaces of cavities in many organs. For example, such epithelial layers include; the simple squamous epithelium lining the air sacs of lungs; the simple columnar epithelium located in bronchi, uterine tubes, and the uterus (all three being classed as ciliated tissues), and the digestive tract and bladder (which two are classed as smooth, non-ciliated tissues); pseudostratified columnar epithelium lining the trachea and much of the upper respiratory tract; stratified squamous epithelium lining the oesophagus, mouth and vagina; stratified columnar epithelium lining the male urethra; and the transitional epithelium lining the bladder, uretha, and ureters.

For example, the epithelial layer may be any layer that the compound of formula (I) can be administered to the epithelial layer by administration to the mouth (e.g., sublingual administration), nose (e.g. intranasal), eyelids (subconjunctival), rectum, trachea (endotracheal), lungs (pulmonary), stomach (gastric), intestines (enteral), ureters (ureteral), urethra (uretheral) or urinary bladder (vesical) of the patient.

For the avoidance of doubt, it is envisaged that the route of administration may be gastrointestinal. When administering gastrointestinally, this may be done through a catheter placed in the urinary tract, the bladder, the stomach, the small intestine or the large intestine. Alternatively, when administering gastrointestinally then the compound of formula (I) may be delivered as a depot capsule or tablet, optionally in the form of a pharmaceutical formulation as disclosed herein.

Particular epithelial layers that the compound of formula (I) may be administered to include cutaneous membranes, serous membranes, cutaneous membranes, synovial membranes and mucous membranes.

The term "subcutaneous injection" refers to injecting the compound with a needle under the skin. The compound of formula (I) may be injected to the cutis or subcutis of a patient, from where the compound diffuses into the blood circulation.

The term "intramuscular injection" refers to injecting the compound with a needle to the muscle of a patient. The compound of formula (I) may be injected to a skeletal muscle, cardiac muscle or smooth muscle of a patient, from where the compound diffuses into the blood circulation.

As used herein, the term "administered to an epithelial layer" refers to the application of the compound of formula (I) to the surface of an epithelial layer of a patient either directly or indirectly. That is to say, the compound of formula (I) may be applied to the surface of an epithelial layer of the patient and the compound of formula (I) crosses the epithelial layer and reaches the pulmonary circulation and/or systemic circulation of the patient.

Depending on the route of administration, the compound may be applied in various forms, for example as a liquid, gel or lotion, or as a vapour if the route of administration is inhalation. Furthermore, the compound of formula (I) may be delivered as a depot capsule or tablet, preferably in the form of a composition as disclosed herein.

For example, if the route of administration is inhalation then the compound of formula (I) can be administered to the epithelial layer in any one of the mouth, nose, trachea, or lungs. The same would apply to a gel comprising the compound of formula (I) that was applied intranasally to the nasal mucous membrane, as although it is applied to the nasal mucous membrane, the compound of formula (I) can still reach the epithelial layers in the mouth, nose, trachea, or lungs of the patient.

For the avoidance of doubt, after administration the compound may remain on the surface of the epithelial layer, or it may absorb into and pass through the surface to underlying tissues.

Similarly, if the route of administration is subcutaneously or intramuscular the compound can be administered to the cutis or subcutis as well as a muscle of a patient. The compound may remain in the cutis, subcutis or muscle, or it may absorb into surrounding tissues before being absorbed into the blood circulation of the patient and finally reaching the pulmonary circulation.

In all aspects of the invention, the administration step may be done subcutaneously, intramuscularly, sublingually, intranasally, intravesically or via inhalation.

Furthermore, the administration step may be done by application to the dermal layer, of a patient. When being applied to the dermal layer of a patient, this may be done by applying the compound as a liquid, cream, lotion or gel to the skin of a patient, for example the liquid, cream, lotion or gel may be soaked into a substrate (e.g. a compress) and applied to the skin of the patient. The substrate may be composed of any material that holds the compound, such as a pad, gauze, patch or sponge.

In each of the first to third aspects of the invention, the administration is in particular to a mucous membrane, with the compound remaining on the surface or passing through (e.g., transmucosal administration). It is particularly surprising that the compound of formula (I) survives the relatively high water content and high amounts of reactive oxygen species present in, on and around epithelial layers, including mucous membranes, and that the compound of formula (I) is not inactivated and is able to provide a biological effect. It is also surprising that the compound of formula (I) survives contact with tissues with cells comprising heme-containing protein and sulfhydryl groups that typically react instantaneously with NO.

Particular mucous membranes that may be mentioned include those in the mouth (e.g., sublingual administration), nose (e.g. intranasal), eyelids (subconjunctival), trachea (endotracheal), lungs (pulmonary), small intestines, large intestines, stomach (gastric), the rectum (rectal mucosa via rectal administration), renal pelvis (by use of nephrostomy tubing) ureters (ureteral), urethra (uretheral) or urinary bladder (vesical) of the patient.

In particular, the administration is to a mucous membrane in the lungs, wherein the administration is via inhalation. In other words, the administration is pulmonary administration by inhalation. In this embodiment, as the administration is via inhalation, it is also envisaged that at least a portion of the compound of formula (I) may be administered to mucous membranes in the mouth, nose and trachea, as well as the lungs.

By the term "inhalation" it is envisaged that the compound of formula (I) is inhaled as a vapour or an aerosol through the nose and/or mouth. Furthermore, inhalation may also be through a nasal or tracheal catheter, an endotracheal tube or a supraglottic airway device.

In a particular embodiment, the administration is to a nasal mucous membrane, wherein administration is via applying a gel or liquid directly to the nasal cavity of the patient. In this embodiment, although the compound of formula (I) is administered directly to the mucous membrane in the nasal cavity, through dispersion in the body it is envisaged that the compound of formula (I) reaches other epithelial layers of the patient, in particular the epithelial layers in the mouth, nose, trachea, or lungs of the patient.

In an embodiment, for nasal administration the compound of formula (I) may be applied as a spray or as a gel which is rubbed against the mucosal surface.

In a particular embodiment, the administration is subcutaneous, wherein the administration is via applying a gel or liquid to the cutis or subcutis of the patient. In this embodiment, the compound of formula (I) may be injected to the cutis or subcutis with a syringe.

In a particular embodiment, the administration is intramuscular, wherein the administration is via applying a gel or liquid to a muscle of the patient. In this embodiment, the compound of formula (I) may be injected to the muscle with a syringe. In an embodiment, via intramuscular administration the compound of formula (I) is administered to is a skeletal muscle, smooth muscle or cardiac muscle.

A particular compound of the first and/or second aspect of the invention is a compound according to formula (II)

(II)

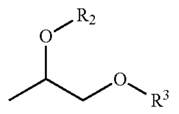

wherein $R^2$ and $R^3$ each independently represent H or —NO, provided that at least one of $R^2$ and $R^3$ represents —NO.

Two enantiomers of the compound according to formula (II) exist, being the R and S form as depicted below:

(II)

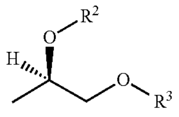

R form (II)

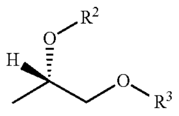

S form

The compounds of formula (I) may contain an asymmetric carbon atom as outlined above and will therefore exhibit optical isomerism.

All stereoisomers and mixtures thereof of the compounds according to formula (I) are included within the scope of the invention.

A further particular compound of the first and/or second aspect of the invention is a compound according to formula (III):

(III)

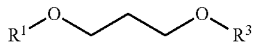

wherein $R^1$ and $R^3$ each independently represent H or —NO, provided that at least one of $R^1$ and $R^3$ represents —NO.

A further particular compound of the first and/or second aspect of the invention is a compound according to formula (IV):

(IV)

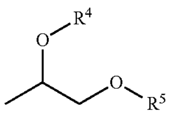

wherein $R^4$ and $R^5$ each independently represent H or —NO, provided that at least one of $R^4$ and $R^5$ represents —NO.

As used herein in relation to the second aspect of the invention, references to "substantially non-aqueous" will refer to the component comprising less than 1% (such as less than 0.5% or less than 0.1%, e.g. less than 0.05%, less than 0.01%) by weight of water.

Particular substantially non-aqueous compositions of the invention that may be mentioned include those wherein the composition comprises from about 0.01% to about 9% (e.g. about 0.01% to about 5%, such as about 3% to about 5%, or about 5% to about 7%) by weight of the one or more of the compounds of the invention (i.e. compounds of formula I).

Particular substantially non-aqueous compositions of the invention that may be mentioned include those wherein the composition comprises from about 1 to about 1000 mM (e.g. about 5 to about 750 mM, such as about 5 to about 500 mM, or about 10 to about 203 mM) of the one or more of the compounds of the invention (i.e. compounds of formula I).

For the avoidance of doubt, the unit mM refers to the concentration of the compound of formula (I) in the non-aqueous composition in $10^{-3}$ mol/L and, where the composition comprises a mixture of compounds of formula I, is based on the average molecular weight of the compounds of formula I in the composition.

Particular substantially non-aqueous compositions of the invention that may be mentioned include those wherein the composition comprises a compound according to formula (II). Preferably the compound according to formula (II) is the S form.

The S form of the compound according to formula (II) is preferred as this has a higher rate of metabolism than the R form. Furthermore, the S form has a different metabolic degradation route, which results in metabolites which are less toxic than those from the R form.

Particular substantially non-aqueous compositions of the invention that may be mentioned include those wherein the composition comprises a compound according to formula (III).

Preferably the compound according to formula (II) is the S form, although it is envisaged that the product is a mixture of both the S and R form of formula (II) with the S form preferably being present in an enantiomeric excess (ee).

In particular embodiments, the compound according to formula (II) may be in an enantiomeric excess of the S form of the compound. That is to say, greater than 50 ee % of the product is in the S form, such as greater than, or equal to, 60 ee %, 70 ee %, 80 ee %, 90 ee %, 95 ee % or 98 ee % of the product is the S form.

In an embodiment where the product is a mono-nitrosylated compound according to formula (II), greater than 50 wt. % of the product is nitrosylated in the 2 position (i.e. $R^2$ is —NO), such as between about 55 wt. % and about 80 wt. % is nitrosylated in the 2 position, for example between about 55 wt. % and 75 wt. %.

Particular substantially non-aqueous compositions that may be mentioned include those wherein the composition consists essentially of one or more compounds of formula I and corresponding compounds of formula I but wherein $R^1$, $R^2$ and $R^3$ represent H (i.e. 1,2-propanediol and/or 1,3-propanediol).

Other particular substantially non-aqueous compositions may comprise (or, particularly, consist essentially of or, more particularly, consist of) one or more compounds of formula II and 1,2-propanediol.

Equally, further substantially non-aqueous compositions may comprise (or, particularly, consist essentially of or, more particularly, consist of) one or more compounds of formula III and 1,3-propanediol.

By the term "consist essentially of", this means that at least 90 wt. % of the defined feature is present, such as at least 95 wt. %, 96 wt. %, 97 wt. %, 98 wt. % or 99 wt. % of the defined feature is present.

Furthermore, particular substantially non-aqueous compositions that may be mentioned include those wherein the composition comprises (or, particularly, consists essentially of or, more particularly, consists of) one or more compounds of formula (II) and (III) along with 1,2-propanediol and 1,3-propanediol.

Particular substantially non-aqueous compositions that may be mentioned include those wherein the composition is substantially free of dissolved nitric oxide.

By the term "substantially free", this means that the non-aqueous compositions of the invention comprise less than 5 wt. %, 4 wt. %, 3 wt. %, 2 wt. % or 1 wt. % of dissolved nitric oxide, such as less than 0.5 wt. % or 0.1 wt. %.

Furthermore, particular substantially non-aqueous compositions may comprise:

(a) one or more compounds of formula IV (IV)

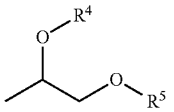

wherein $R^4$ and $R^5$ each independently represent H or —NO, provided that at least one of $R^4$ and $R^5$ represents —NO; and (b) 1,2-propanediol.

The substantially non-aqueous compositions may be administered alone or may be administered by way of known pharmaceutical compositions/formulations.

Accordingly, the substantially non-aqueous composition may be comprised in a pharmaceutical formulation, optionally wherein the pharmaceutical formulation comprises one or more pharmaceutically acceptable excipients.

The skilled person will understand that references herein to pharmaceutical formulations herein refer to the substantially non-aqueous composition in the form of a pharmaceutical formulation and will include references to all embodiments and particular forms thereof.

As used herein, the term pharmaceutically-acceptable excipients includes references to vehicles, adjuvants, carriers, diluents, pH adjusting and buffering agents, tonicity adjusting agents, stabilizers, permeability enhancers, wetting agents and the like. In particular, such excipients may include adjuvants, diluents or carriers.

Particular pharmaceutical formulations that may be mentioned include those wherein the pharmaceutical formulation comprises at least one pharmaceutically acceptable excipient.

Particular pharmaceutical formulations that may be mentioned include those wherein the one or more pharmaceutically acceptable excipients are substantially non-aqueous.

For the avoidance of doubt, references herein to compounds of formula (I) for particular uses may also apply to compositions and pharmaceutical formulations comprising compounds of the invention, as described herein.

Devices for Administering Compounds of Formula (I) via Inhalation

The compounds of formula (I) are particularly useful in the treatment of a condition wherein NO has a beneficial effect, wherein administration is to an epithelial layer of a patient via inhalation.

Therefore, in a third aspect of the invention there is provided a device for administering a substantially non-aqueous composition as defined in the second aspect of the invention to a patient, wherein the administration is via inhalation.

Use of the device for administration via inhalation may be inhalation through the mouth, nose, or both. As outlined above, administration by inhalation may in particular be to an epithelial layer (e.g. a mucous membrane) in the lungs, wherein the administration is via inhalation. In other words, the administration is pulmonary administration by inhalation.

The device may be used in conjunction with a nasal catheter, a tracheal catheter, an endotracheal tube or supraglottic airway device for administering via inhalation.

As the administration is via inhalation, it is also envisaged that at least a portion of the compound of formula (I) may be administered to mucous membranes in the mouth, nose and/or trachea, as well as the lungs via use of the device.

The device may be hand-held so that the patient may self-administer the substantially non-aqueous composition, or it may be in the form of a ventilator that a qualified medical practitioner operates.

In a particular embodiment, the device comprises a vaporiser element and/or an atomiser element for vaporising or atomising the substantially non-aqueous composition.

In an embodiment, the device is configured for connecting to a nasal catheter, a tracheal catheter, an endotracheal tube or a supraglottic airway device.

As used herein the term "vaporiser element" refers to an element within the device that enables the substantially non-aqueous composition to be heated to form a vapor, i.e. the device converts at least a portion of the non-aqueous composition from a liquid to a gas so that the patient may inhale it.

In a particular embodiment, the vaporiser element may be in the form of a heating element that in use heats the substantially non-aqueous composition thus vaporising it and allowing for it to be inhaled by the user.

In an embodiment, in use the heating element heats to a temperature of from about 100 to about 350° C., such as from about 100 to about 250° C., for example from about 190 to about 235° C.

In an embodiment, the heating element heats the substantially non-aqueous composition to a temperature of from about 100 to about 350° C., such as from about 100 to about 250° C., for example from about 190 to about 235° C.

As used herein the term "atomiser element" refers to an element within the device which enables the substantially non-aqueous composition to be inhaled by the user as a fine mist or spray. Such atomiser elements may also be referred to as nebulizers.

Optionally the device comprises a reservoir, such as a cartridge, for containing the substantially non-aqueous composition. The cartridge is preferably removable so as to allow the cartridge to be removed once empty and replaced with a full cartridge, allowing the device to be reused.

In an embodiment, the reservoir is configured to contain from about 0.5 to about 10 ml of the substantially non-aqueous composition, such as from about 0.5 to about 5 ml, for example from about 1 to about 3 ml of the substantially non-aqueous composition.

Advantageously, the device is an electronic cigarette, wherein such a device comprises:

a. a reservoir for containing the substantially non-aqueous composition;
b. a vaporiser for vaporising the substantially non-aqueous composition;
c. a mouthpiece;
d. a battery;
e. a microprocessor; and
f. a sensor for detecting when a user inhales on the mouthpiece.

The reservoir may be in the form of a cartridge containing the substantially non-aqueous composition, and the cartridge may be removable. Therefore, the device may also comprise a wick element configured to transfer heat from the heating element to the substantially non-aqueous composition in the cartridge.

The heat transfer may be directly from the wick itself (e.g. the wick element penetrates into the cartridge directly to contact the substantially non-aqueous composition) and/or the cartridge may comprise conductive elements which, when in place in the device, contact the wick element so as to allow transfer of heat from the wick to the substantially non-aqueous composition.

In an embodiment, the electronic cigarette is an eGo AIO cigarette (Joyetech® (Shenzhen) Electronics Co, Ltd., China).

In a fourth aspect of the invention, there is provided a cartridge for use with the device as defined in the third aspect of the invention, wherein the cartridge comprises a substantially non-aqueous composition as defined in the second aspect of the invention.

In an embodiment, the cartridge comprises from about 0.5 to about 10 ml of the substantially non-aqueous composition, such as from about 0.5 to about 5 ml, for example from about 1 to about 3 ml of the substantially non-aqueous composition.

Processes for Preparing the Compounds of Formula (I)

Also described herein is a process for the preparation of a composition comprising one or more compounds of formula I (I)

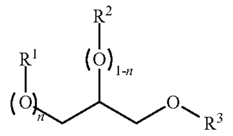

wherein:

$R^1$, $R^2$ and $R^3$ each independently represent H or —NO;

n is 0 or 1;

wherein when n is 0 then $R^1$ is H, and when n is 1 the $R^2$ is H; and provided that at least one of $R^1$ $R^2$ and $R^3$ represents —NO, said process comprising the step of:

(i) reacting a corresponding compound of formula I but wherein $R^1$, $R^2$ and $R^3$ represent H with a source of nitrite, optionally in the presence of a suitable acid, wherein:

(a) when the source of nitrite is an organic nitrite, step (i) is performed in a suitable organic solvent; and (b) when the source of nitrite is an inorganic nitrite, step (i) is performed in a bi-phasic solvent mixture comprising an aqueous phase and a non-aqueous phase.

For the avoidance of doubt, the product of the process (i.e. the compound of formula I) may also (or instead) be referred to as a mono- and bis-nitrosylated 1,2-propanediol or 1,3-propanediol (or a mixture of such compounds, i.e. a composition comprising one or more mono- or bis-nitrosylated 1,2- or 1,3-propanediol).

For the avoidance of doubt, the corresponding compound of formula I, but wherein $R^1$, $R^2$ and $R^3$ represent H, may be referred to as a corresponding 1,2-propanediol and/or 1,3-propanediol (i.e. corresponding to the structure of the desired product), which may in turn be referred to as the starting material for the process of the invention. Put another way, the corresponding compound of formula I may be a compound according to formula (Ia) as defined below.

(Ia)

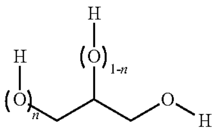

For the avoidance of doubt, where the integer (n or 1-n) as relating to the oxygen atoms is 0, no oxygen atom is present and the substituent $R^1$ and $R^2$ (and the corresponding H in the compound of formula (Ia)) is bonded to the respective carbon.

The skilled person will understand that references herein to the process will include references to all embodiments and particular features thereof.

The skilled person will understand that references to the preparation of a composition comprising one or more compounds of formula (I) will refer to the preparation of a composition that contains, as a constituent part, an amount of one or more compounds the structure of which is as defined in formula I, optionally together with other compounds. The process may also be referred to a process for preparing compounds of formula I (i.e. a process for preparing one or more compounds of formula I).

The skilled person will understand that references to the process being a process for preparing compounds of formula I will be understood to indicate that the process may result in the preparation of one or more types of compound each as described by formula I as defined herein (e.g. where more than one such compound is present, as a mixture thereof).

As such, the skilled person will also understand that the compounds formed in the process may take the form of a mixture of each mono-nitrite and the di-nitrite products, with the relative amounts of each varying depending on the concentration of compounds of formula I.

In particular, the process may allow for the preparation of a composition wherein at least 50 wt. %, 60 wt. %, 70 wt. % or 80 wt. % (such as at least 90 wt. % or at least 99 wt. %, e.g. at least 99.9 wt. %) of the compounds of formula I are mono-nitrosylated, such that $R^1$, $R^2$ and $R^3$ each independently represent H or —NO, provided that one of $R^1$, $R^2$ or $R^3$ represents —NO and the other groups represent H.

In particular, the process may result in the preparation of the composition that comprises one or more compounds of formula I together with one or more corresponding compounds of formula I but wherein $R^1$, $R^2$ and $R^3$ represent H (i.e. 1,2-propanediol and/or 1,3-propanediol, e.g. unreacted 1,2-propanediol and/or 1,3-propanediol starting material), and optionally other compounds.

In certain embodiments, the process may be a process for preparing a composition consisting essentially of one or more compounds of formula I, and one or more corresponding compounds of formula I but wherein $R^1$, $R^2$ and $R^3$ represent H (i.e. 1,2-propanediol and/or 1,3-propanediol; e.g. as a mixture thereof).

The skilled person will understand that the term "reacting" will refer to bringing the relevant components together in a manner (e.g. in suitable state and medium) such that a chemical reaction occurs. In particular, the reference to reacting the starting material (i.e. 1,2-propanediol and/or 1,3-propanediol) with a source of nitrite will refer to a chemical reaction between the starting material and the nitrite (i.e. the nitrite provided by the source of nitrite).

The skilled person will understand that the reference to "a source of nitrite" may instead refer simply to "nitrite", as it is the nitrite provided by the source of nitrite which undergoes chemical reaction. As such, references to a source of nitrite will be understood to refer to a compound that provides, for reaction, a nitrite moiety (which may be present either in ionic or covalently bonded form, depending on the source of nitrite present). The source of nitrite may therefore be referred to as a source of reactive (or reactable) nitrite (or nitrite moiety). For the avoidance of doubt, the source of nitrite may be an inorganic nitrite or an organic nitrite.

As indicated herein, when the source of nitrite is an organic nitrite, step (i) is performed in a suitable organic solvent.

The skilled person will understand that various organic nitrites may be used in the process of the invention, such as alkyl nitrites.

Particular alkyl nitrites that may be mentioned include ethyl nitrite, propyl nitrites, butyl nitrites and pentyl nitrites. In particular embodiments, the alkyl nitrite is n-butyl nitrite, isobutyl nitrite or tert-butyl nitrite, such as tert-butyl nitrite.

Where the source of nitrite is an organic nitrite, the skilled person will be able to select a suitable solvent. For example, suitable solvents may include those referred to herein as suitable organic components of a biphasic solvent system, and mixtures thereof.

For the avoidance of doubt, unless specified otherwise, the references to the process of the invention being performed in a suitable organic solvent do not indicate that other non-organic solvents, such as water, may be present.

In a particular embodiment, where the process is performed in a suitable organic solvent, the solvent may be essentially water free (which may be referred to as a being "water free" or "dry"), which may indicate that the solvent contains less than about 1% (e.g. less than about 0.1%, such as less than about 0.01%) by weight of water.

The term "about" is defined, herein, as meaning that the defined value may deviate by ±10%, such as by ±5%, for example by ±4%, ±3%, ±2%, or ±1%. The term "about" can be removed from throughout the specification without departing from the teaching of the invention.

As indicated herein, when the source of nitrite is an inorganic nitrite, step (i) is performed in a bi-phasic solvent mixture comprising an aqueous phase and a non-aqueous phase.

The skilled person will understand that the term "biphasic solvent mixture" as used herein will refer to a system comprised of two solvents or solvent mixtures which do not mix to form a single solvent phase but instead are present as two distinct (i.e. non-mixed) phases.

Where such solvent mixtures comprise water and an organic solvent (or mixture of organic solvents) such solvent systems may be said to comprise an "aqueous phase" and an "organic phase". For the avoidance of doubt, the term bi-phasic does not indicate that substances forming other phases, such as substances forming a solid phase, may be present in addition to the solvent system (that is to say, other phases may also be present).

Particular sources of inorganic nitrites that may be mentioned include metal nitrites, such as alkali metal nitrites and alkaline earth metal nitrite. Ionic liquids may also be a suitable source of inorganic nitrites.

For the avoidance of doubt, the term alkali metal takes its usual meaning in the art, namely referring to IUPAC group 1 elements and cations, including lithium, sodium, potassium, rubidium, caesium and francium.

For the avoidance of doubt, the term alkaline earth metal takes its usual meaning in the art, namely referring to IUPAC group 2 elements and cations, including beryllium, magnesium, calcium, strontium, barium and radium.

More particular inorganic nitrites that may be mentioned include alkali metal nitrites, such as lithium nitrite, sodium nitrite and potassium nitrite. In a particular embodiment, the source of nitrite is sodium nitrite.

Alternatively, the metal nitrite may be an alkaline earth metal nitrite, such as lithium nitrite, magnesium nitrite or calcium nitrite.

For the avoidance of doubt, the skilled person will understand that the non-aqueous phase in the bi-phasic solvent system may be an organic solvent, which may therefore be referred to as an organic phase.

The skilled person will be able to select a suitable non-aqueous (i.e. organic) solvent based on the properties of the aqueous phases. For example, where the aqueous phase has a certain level of substances dissolved therein (e.g. ionic solids, such as salts), a wide-range of organic solvents may be selected in order to form a bi-phasic solvent system.

In particular embodiments, the non-aqueous phase consists of a water immiscible organic solvent. In more particular embodiments, the water immiscible organic solvent is an aprotic organic solvent.

Particular water immiscible organic solvents (i.e. particular solvents forming the non-aqueous phase) that may be mentioned include ethers (e.g. tert-butyl methyl ether, cyclopentyl methyl ether, methyl tetrahydrofuran, diethyl ether, diisopropyl ether) and dichloromethane (DCM).

More particular water immiscible organic solvents (i.e. particular solvents forming the non-aqueous phase) that may be mentioned include dichloromethane, diethyl ether and tert-butyl methyl ether. In more particular embodiments, the water immiscible organic solvent is tert-butyl methyl ether.

In certain embodiments that may be mentioned, the solvent mixture may comprise excess compounds of formula I but wherein $R^1$, $R^2$ and $R^3$ represent H (i.e. 1,2-propanediol and/or 1,3-propanediol). For the avoidance of doubt, in such circumstances, the 1,2-propanediol and/or 1,3-propanediol (i.e. the compounds of formula I but wherein $R^1$, $R^2$ and $R^3$ represent H) may be present as both a solvent (e.g. a component of a solvent mixture) and a reagent. As such, in particular embodiments, the process is a process for preparing compounds of formula I as a solution in corresponding compounds of formula I but wherein $R^1$, $R^2$ and $R^3$ represent H, i.e. 1,2-propanediol and/or 1,3-propanediol (e.g. in the form of a mixture comprising 1,2-propanediol and/or 1,3-propanediol, as appropriate). In certain embodiments, when the source of nitrite is an organic nitrite, the solvent may consist essentially of compounds of formula I but wherein $R^1$, $R^2$ and $R^3$ represent H (i.e. 1,2-propanediol and/or 1,3-propanediol). That is to say, the compounds of formula I but wherein $R^1$, $R^2$ and $R^3$ represent H may act both as solvent and as reactant.

In an alternative embodiment, when the source of nitrite is an inorganic nitrite, step (i) may be performed in a single solvent, wherein the solvent may consist essentially of compounds of formula I but wherein $R^1$, $R^2$ and $R^3$ represent H (i.e. 1,2-propanediol and/or 1,3-propanediol). That is to say, the compounds of formula I but wherein $R^1$, $R^2$ and $R^3$ represent H may act both as solvent and as reactant.

In alternative embodiments, the process of the invention may be performed with an excess of nitrite relative to the starting material of formula I but wherein $R^1$, $R^2$ and $R^3$ represent H (i.e. 1,2-propanediol and/or 1,3-propanediol).

As used herein, the term "excess" will take its usual meaning in the art, namely indicating that the component is present in a greater than stoichiometric amount for the reaction in which it is a reagent.

As indicated herein, the process (in particular, the reaction between components) is optionally performed in the presence of a suitable acid.

Particular processes that may be mentioned include those wherein the step of reacting the starting material (i.e. 1,2-propanediol and/or 1,3-propanediol) with a source of nitrite is carried out in the presence of a suitable acid.

Particular acids that may be mentioned as suitable acids include Brønsted acids (i.e. proton donor acids), more particularly wherein such acids may be referred to as a strong acid.

For the avoidance of doubt, the term "strong acid" takes its usual meaning in the art, referring to Brønsted acids whose dissociation is substantially complete in aqueous solution at equilibrium. In particular, references to strong acids may refer to Brønsted acids with a pKa (in water) of less than about 5 (for example, less than about 4.8). For the avoidance of doubt, for multiprotic acids, such as sulphuric acid, the term strong acid refers to the dissociation of the first proton.

Certain strong acids that may be mentioned include those with a pKa (in water) of less than about 1, such as less than about 0 (e.g. less than about −1 or −2). For example, strong acids that may be mentioned include those with a pKa (in water) of about −3. The skilled person will understand that suitable acids may include non-nucleophilic acids, as known to those skilled in the art.

Particular suitable acids that may be mentioned include sulphuric acid, phosphoric acid, trifluoroacetic acid and acetic acid.

More particular suitable acids that may be mentioned include mineral acids (e.g. strong mineral acids), such as sulphuric acid.

The skilled person will be able to select suitable amounts of reagents to use in the process within the teaching herein. For example, the ratio (i.e. the molar ratio) of corresponding compound of formula I but wherein $R^1$, $R^2$ and $R^3$ represent H to nitrite to acid (where present) may be about 1:from about 1 to about 5:to about 0.5 to about 3.5, for example about 1:from about 1 to about 3:from about 0.5 to about 2 (such as about 1:4:2.7, or about 1:2:0.95, or about 1:2:1). For the avoidance of doubt, where a suitable acid is not present, the ratios between the corresponding compound of formula I but wherein $R^1$, $R^2$ and $R^3$ represent H and nitrite may still apply.

In particular embodiments, process step (i) is carried out at a temperature of from about −30° C. to about 5° C., such as from about −30° C. to about 0° C., for example from about −30° C. to about −10° C., preferably from about −25° C. to about −15° C.

In particular embodiments, process step (i) is carried out under an inert atmosphere, such as a nitrogen or argon atmosphere, preferably an argon atmosphere. Furthermore, in particular embodiments any steps of the process may be carried out under an inert atmosphere, such as a nitrogen or argon atmosphere, preferably an argon atmosphere.

Particular processes that may be mentioned, particularly in which a bi-phasic solvent system is used, include those wherein the process further comprises, after (e.g. directly following) step (i), the step of:

(ii) removing substantially all of the aqueous phase (i.e. removing substantially all water) from the solvent mixture.

The skilled person will appreciate that the aqueous phase may be removed from the solvent mixture by any suitable process and using any suitable equipment as known in the art (for example, by using a separating funnel or similar apparatus).

As used herein, unless otherwise specified the term "substantially all" will refer to at least 80% (e.g. at least 85%, at least 90%, or at least 95%, such as at least 99%) of the specified substance(s), according to the relevant measure (e.g. by weight thereof).

The skilled person will also understand that references to "removing substantially all of the aqueous phase from the solvent mixture" may be replaced with references to "removing some or all of the aqueous phase from the solvent mixture" or simply "removing the aqueous phase from the solvent mixture".

For the avoidance of doubt, in the context of its removal, the term aqueous phase will refer to the (separate) phase formed from water and components dissolved therein.

Particular processes that may be mentioned, particularly in which a bi-phasic solvent system is used, include those wherein the process further comprises, after (e.g. directly following) step (i), the steps of (in the sequence shown):

(ii) removing some or all (e.g. substantially all) of the aqueous phase (i.e. of water);

(iii) washing the remaining organic phase with one or more further aqueous phase;

(iv) optionally repeating steps (ii) and (iii) one or more times.

Further processes that may be mentioned, particularly in which a bi-phasic solvent system is used, include those wherein the process further comprises, after (e.g. directly following) step (i), the steps of (in the sequence shown):

(ii) removing some or all (e.g. substantially all) of the aqueous phase (i.e. of water);

(iii) washing the remaining organic phase with one or more further aqueous phase;

(iv) optionally repeating steps (ii) and (iii) one or more times;

(v) optionally reducing (i.e. reducing the amount/volume of) the organic phase, such as by removal some or substantially all of the water immiscible organic solvent (e.g. organic solvent other than 1,2 propanediol and/or 1,3-propanediol), and (vi) optionally drying the product, wherein steps (ii) to (vi) may be performed in any order provided that steps (ii) to (iv) are performed before steps (v) and (vi).

In particular embodiments, process steps (ii) to (iv) may be carried out at a temperature of from about −20° C. to about 5° C., such as from about −10° C. to about 5° C.

In particular embodiments, process step (v) may be carried out at a temperature of from about 0° C. to about 30° C., such as from about 10° C. to about 30° C., for example from about 15° C. to about 30° C.

In particular embodiments, process step (v) is carried out for no more than 6 hours, for example no more than 5 hours, preferably no more than 4 hours.

In particular embodiments, each of steps (ii) to (vi) are performed, such as wherein those steps are performed in the order indicated.

For the avoidance of doubt, the skilled person will understand that washing the remaining organic phase with one or more further aqueous phase will refer to steps comprising: adding a further portion of aqueous solvent (e.g. water); mixing with the (separate) organic phase (e.g. by stirring and/or shaking together); and removing substantially all of the aqueous phase, and optionally repeating said steps one or more times.

The skilled person will understand that step (iii) may be performed by any suitable process and using any suitable equipment known in the art (for example, using a separating funnel).

The skilled person will understand that step (v) may be performed by any suitable process and using any suitable equipment known in the art (for example, by evaporation under reduced pressure).

In the context of step (v), references to removal of the some of the organic phase may refer in particular to removal of substantially all of the water immiscible organic solvent, as defined herein. More particularly, removal of the water immiscible organic solvent may refer to removal of at least 99% (such as at least 99.5%, 99.9% or, in particular, 99.99%) by weight of the water immiscible organic solvent.

Such removal of the water immiscible organic solvent may also refer to removal such that the product following such removal contains less than 1% (such as less than 0.5%, 0.1%, e.g. less than 0.05%, less than 0.01%) by weight of the water immiscible organic solvent.

For the avoidance of doubt, in the context of step (v), references to removal of the organic phase, such as the water immiscible organic solvent, will refer to the removal of any such solvents as defined herein (e.g. the removal of dichloromethane or tert-butyl methyl ether). Where further organic solvents are present (such as those which are not water immiscible, e.g. excess 1,2-propanediol and/or 1,3-propanediol acting as a solvent) a portion of such solvents may be also removed (e.g. together with a water immiscible organic solvent).

In the context of steps (vi), references to drying the product will refer to the removal of water from the material remaining after preceding steps. Such removal of water may refer to removal such that the product following such drying contains less than 1% (such as less than 0.5% or less than 0.1%, e.g. less than 0.05% or less than 0.01%) by weight of water.

The skilled person will understand that step (vi) may be performed by any suitable process and using any suitable equipment known in the art (for example, by contacting the remaining organic phase with a suitable drying agent, such as anhydrous sodium sulphate, anhydrous magnesium sulphate and/or molecular sieves).

Particular processes that may be mentioned include those wherein the process further comprises the step (e.g. after step (i) and, if present, other steps as described herein) of adding a further amount of corresponding compound of formula I but wherein $R^1$, $R^2$ and $R^3$ represent H (i.e. 1,2-propanediol and/or 1,3-propanediol), such that the combined mixture of the one or more compounds of formula I and corresponding compounds of formula I but wherein $R^1$, $R^2$ and $R^3$ represent H (i.e. 1,2-propanediol and/or 1,3-propanediol) comprises from about 0.01% to about 9% (e.g.

about 0.01% to about 5%, such as about 3% to about 5%, or about 5% to about 7%) by weight of the one or more of the compounds of the invention.

As outlined above, all embodiments of the process and particular features mentioned herein may be taken in isolation or in combination with any other embodiments and/or particular features mentioned herein (hence describing more particular embodiments and particular features as disclosed herein) without departing from the disclosure of the process.

For example: the process step (i) being carried out at a temperature of from about −30° C. to about 5° C. may be combined with the feature of the process steps (ii) to (iv) may be carried out at a temperature of from about −20° C. to about 5° C.; the feature of the process step (v) being carried out at a temperature of from about 0° C. to about 30° C.; and/or the feature of process step (v) being carried out for no more than 6 hours.

More particular processes that may be mentioned include those wherein the parameters specified are in accordance with the examples provided herein.

A particular product of the process is a compound according to formula (II)

(II)

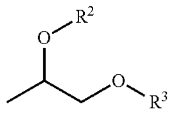

wherein $R^2$ and $R^3$ each independently represent H or —NO, provided that at least one of $R^2$ and $R^3$ represents —NO, wherein the process comprises the step of reacting 1,2-propanediol (i.e. the starting material) with a source of nitrite, under conditions as described herein (including all embodiments thereof).

Two enantiomers of the compound according to formula (II) exist, being the R and S form as depicted below:

(II)

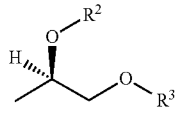

R form (II)

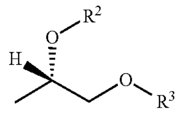

S form

A further particular product of the process is a compound according to formula (III) as depicted below:

(III)

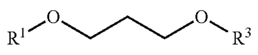

wherein $R^1$ and $R^3$ each independently represent H or —NO, provided that at least one of $R^1$ and $R^3$ represents —NO, wherein the process comprises the step of reacting 1,3-propanediol with a source of nitrite.

The two particular processes depicted above for the production of compounds according to formula (II) and (III) may be carried out together or independently of one another.

Based on the occurring biphasic nature of the reaction mixture, optional addition of a phase-transfer catalyst (PTC) may support the product formation. Common PTCs are for example, but not limited to, tetraalkylammonium ions, such as $Me_4N+$, $Et_4N+$, $Bu_4N+$, or $Bu_3(N+)CH_2PHCl$, with counterions such as =Cl—, Br—, $HSO_4$—, or other types of alkylammonium PTCs such as Aliquat® 336, in substoichiometric amounts of <1 equivalent, for example, but not exclusively, in the range of about 0.05 to about 40 mol %, such as about 0.1 to about 30 mol %, for example of about 0.1 to about 20 mol %.

A further particular product of the process is a compound according to formula (IV) as depicted below (IV)

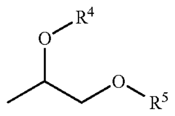

wherein $R^4$ and $R^5$ each independently represent H or —NO, provided that at least one of $R^4$ and $R^5$ represents —NO.

A particular process, therefore, is for the preparation of a composition comprising one or more compounds of formula (IV)

(IV)

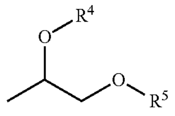

wherein $R^4$ and $R^5$ each independently represent H or —NO, provided that at least one of $R^4$ and $R^5$ represents —NO, said process comprising the step of:

(i) reacting 1,2-propanediol with a source of nitrite, optionally in the presence of a suitable acid, wherein:

(a) when the source of nitrite is an organic nitrite, step (i) is performed in a suitable organic solvent; and (b) when the source of nitrite is an inorganic nitrite, step (i) is performed in a bi-phasic solvent mixture comprising an aqueous phase and a non-aqueous phase.

Any of the process steps outlined herein may be combined with the particular process described above with respect to formula (IV) and particular embodiments are outlined below.

In a particular process the inorganic nitrite is a metal nitrite, optionally wherein the metal nitrite is an alkali metal nitrite or an alkaline earth metal nitrite, preferably an alkali metal nitrite.

In a particular embodiment the alkali metal nitrite is sodium nitrite.

In a further particular embodiment the organic nitrite is an alkyl nitrite, such as tert-butyl nitrite.

In a particular process the suitable acid is a strong acid, such as a strong mineral acid (e.g. sulphuric acid).

In a particular embodiment the non-aqueous phase comprises a water immiscible organic solvent, such as a water immiscible aprotic organic solvent.

In an embodiment the water immiscible organic solvent is dichloromethane.

In a particular process, the solvent mixture further comprises excess 1,2-propanediol.

In a further particular process, after step (i) the process further comprises the step of:

(ii) removing substantially all of the aqueous phase from the solvent mixture.

In an embodiment, after step (i) the process further comprises the step(s) of:

(ii) removing some or all (e.g. substantially all) of the aqueous phase (i.e. of water);

(iii) washing the remaining organic phase with one or more further aqueous phase;

(iv) optionally repeating steps (ii) and (iii) one or more times;

(v) optionally reducing (i.e. reducing the amount/volume of) the organic phase, and (vi) optionally drying the product, wherein steps (ii) to (vi) may be performed in any order provided that steps (ii) to (iv) are performed before steps (v) and (vi).

In a particular embodiment, the process further comprises the step of adding a further amount of 1,2-propanediol, such that the combined mixture of the one or more compounds of formula I and 1,2-propanediol comprises from about 0.01% to about 9% by weight of the one or more compounds of formula IV.

In particular embodiments of the first and second aspect of the invention, the compound of formula (I) is prepared by any one of the processes defined above.

In the process to prepare the compounds, the various stereoisomers may be isolated by separation of a racemic or other mixture of the compounds using convention, e.g. fractional crystallisation or HPLC, techniques. Alternatively, the desired optical isomers may be made by reaction of the appropriate optically active starting materials under conditions which will not cause racemisation (i.e. a 'chiral pool' method), by reaction of the appropriate starting material with a 'chiral auxiliary' which can be subsequently removed at a suitable stage, by derivatisation (i.e. a resolution, including dynamic resolution); for example, with a homochiral acid followed by separation of the diastereomeric derivatives by convention means such as chromatography, or by reaction with an appropriate chiral reagent or chiral catalyst under conditions known to the skilled person.

EXAMPLES

Figure 1:
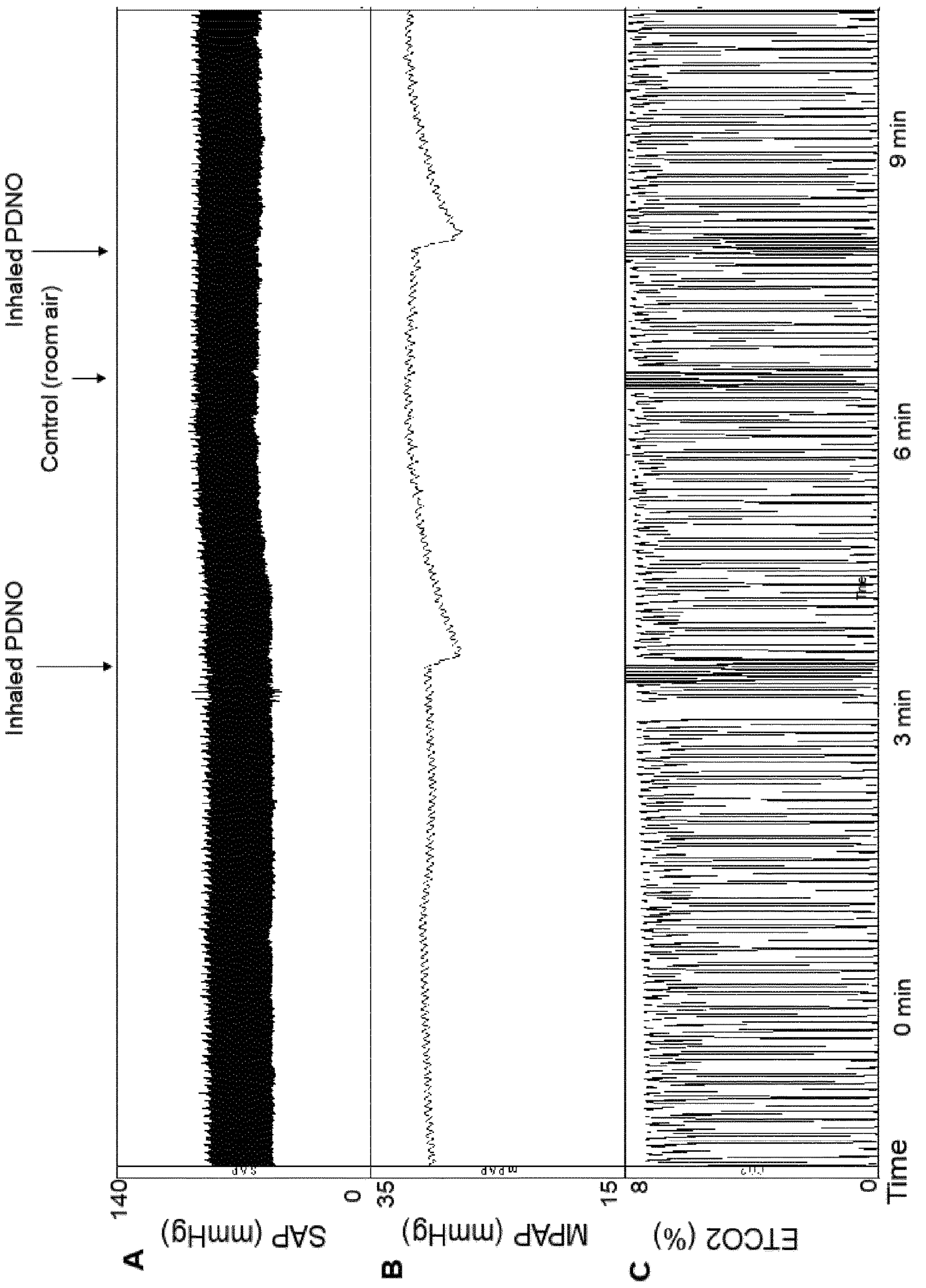
FIG. 1 details the effects of inhaled PDNO administration (by means of an electrical cigarette (eGo AIO, Joyetech), n=1) systemic arterial pressure (SAP, panel A), mean pulmonary arterial pressure (mPAP, panel B) and end-tidal carbon dioxide (ETCO2, panel C) in an anesthetised pig subjected to hypercapnoic aPH. The first and third arrow indicate administration of PDNO, whereas the middle arrow indicates administration of room air.

The invention is illustrated by way of the following examples, which are not intended to be limiting on the general scope of the invention.

Abbreviations aq aqueous
conc concentration
GC gas chromatography
NMR nuclear magnetic resonance
equiv. equivalent(s)
rel. vol. relative volume(s)

For the avoidance of doubt, compounds of formula (I) may also be referred to herein as compounds of the invention and may be referred to by the acronym PDNO, which will indicate that such compounds, including all embodiments and particular features thereof, are used in the methods and uses as described in relation to the present invention. Furthermore, when compositions of PDNO are described that also contain PD, the PD refers to the corresponding propanediol to the compound of formula (I), that is to say the PD is the same compound according to formula (I), but wherein but wherein $R^1$, $R^2$ and $R^3$ represent H.

However, in the context of the examples below, the term "PDNO" specifically refers to compounds according to Formula (II). In conjunction with this, the term "PD" refers specifically to 1,2-propanediol, being the starting material from which PDNO is prepared.

General Procedures

Starting materials and chemical reagents specified in the preparations described below are commercially available from a number of suppliers, such as Sigma Aldrich.

All NMR experiments were performed at 298K on a Bruker 500 MHz AVI instrument equipped with a QNP probe-head with Z-gradients using the Bruker Topspin 2.1 software. Signals were referenced to residual $CHCl_3$ at 7.27 ppm, unless stated otherwise.

Stability Assays

Assays of the stability samples were performed by GC/FID, under the following conditions. 1,4-Dioxane was used as the Internal Standard (IS; approximately 0.50 mg/ml in $CH_3CN$).

GC column: Rxi-5Sil MS, 20 m×0.18 mm, 0.72 μm
Carrier gas: Helium
Inlet: 200° C., split ratio 30:1
Constant flow: 1.0 ml/min
Oven temperature profile: 40° C. (3 min), 10° C./min, 250° C. (3 min)
FID: temp 300° C.; $H_2$ flow 30 ml/min, Air flow 400 ml/min, make-up flow ($N_2$) 25 ml/min

Example 1—Preparation of 1-(nitrosooxy)-propan-2-ol, 2-(nitrosooxy)-propan-1-ol and 1,2-bis(nitrosooxy)propane with sodium nitrite 1,2-propanediol (15 mL, 205 mmol), water (100 mL), dichloromethane (200 mL) and sodium nitrite (57 g, 826 mmol) were added to a 500 mL three-necked round bottom flask. The mixture was cooled down to 0° C. with an ice bath. Concentrated sulphuric acid (30 mL, 546 mmol) and water (30 mL) were added to a dropping funnel and cooled to 5° C. in a refrigerator. The funnel was adapted to the round bottom flask and the acid added to the nitrite mixture during two hours. The mixture was stirred with a magnet for 20 minutes and then poured into a separation funnel together with more dichloromethane (100 mL) and water (100 mL). The organic phase was separated and dried with sodium sulphate, and reduced on a rotavapor to yield a mixture of 1,2-propanediol (3 wt. %), 1-(nitrosooxy)-propan-2-ol (23 wt. %) 2-(nitrosooxy)-propan-1-ol (13 wt. %) and 1,2-bis (nitrosooxy)propane (57 wt. %).

Example 2—Preparation of 1-(nitrosooxy)-propan-2-ol, 2-(nitrosooxy)-propan-1-ol and 1,2-bis(nitrosooxy)propane with sodium nitrite 1,2-propandiol (20 mL, 273.4 mmol), water (60 mL), dichloromethane (120 ml) and sodium nitrite (37.72 g, 546.7 mmol) were added to a 0.5 reactor fitted with a stirrer and flushed with nitrogen and kept during the course of the following reaction under nitrogen. The mixture was cooled down to below 5° C. by cooling the mantle to 0° C. Concentrated sulphuric acid (26.3 g, 260.1 mmol) and water were added to a dropping funnel. The funnel was attached (to the reactor and the acid was added to the nitrite mixture during 33 minutes. The mixture was stirred for 54 minutes and then poured into a flask containing an aqueous saturated sodium bicarbonate solution (100 mL). The mixture was transferred to a separation funnel and the organic phase was washed. The aqueous phase was discarded, and the organic phase was washed with additional aqueous saturated sodium bicarbonate solution (100 mL). The organic phase was dried with magnesium sulphate and then transferred to a 1 L round bottom flask together with 1,2-propandiol (120 ml, 1640 mmol). The solution was reduced on a rotavapor under reduced pressure until the dichloromethane was removed. The removal of dichloromethane was monitored by NMR. A clear solution (134 g) containing 1,2-propandiol (82.8 wt. %), 1-(nitrosooxy)-propan-2-ol (10.4 wt. %), 2-nitrosooxy)-propan-1-ol (6 wt. %) and 1,2-bis(nitrosooxy)propane (0.8 wt. %) was obtained.

$^1$H-NMR, δ ppm: 5.61 (br s 1H), 4.75-5.58 (m, 2H), 4.11 (br s, 1H), 3.90-3.87 (m, 1H), 3.83-3.69 (m, 2H), 3.60 (dd, J=3.0, 11.2 Hz, 1H), 3.38 (dd, J=7.9, 11.2 Hz, 1H), 1.47 (d, J=6.6 Hz, 3H), 1.39 (d, J=6.4 Hz, 3H), 1.26 (d, J=6.4 Hz, 3H), 1.15 (d, J=6.3 Hz, 3H), Signals for CH and $CH_2$ of the 1,2-bis(nitrosooxy)propane were below the detection limit.

Example 3—Preparation of 1-(nitrosooxy)-propan-2-ol, 2-(nitrosooxy)-propan-1-ol and 1,2-bis(nitrosooxy)propane with tert-butyl nitrite Tert-butyl nitrite (2 mL, 15.1 mmol) was added to a round bottom flask with 1,2-propanediol (11 mL, 150.3 mmol) and the obtained solution was stirred at ambient temperature. 1 mL of the reaction solution was then mixed with 7.5 mL 1,2-propanediol.

Example 4—Stability of Non-Aqueous Mixtures of 1-(nitrosooxy)-propan-2-ol, 2-(nitrosooxy)-propan-1-ol and 1,2-propanediol Three different concentrations of 1-(nitrosooxy)-propan-2-ol and 2-(nitrosooxy)-propan-1-ol in 1,2-propanediol were prepared and stored in both a refrigerator (5° C.) and freezer (−20° C.). Aliquots of each solution were taken periodically and analysed by GC to determine the concentration of 1-(nitrosooxy)-propan-2-ol and 2-(nitrosooxy)-propan-1-ol.

The results of the GC analysis are shown in the table below (column: Rxi-5Sil MS, 20 m×0.18 mm, 0.36 film thickness; carrier: He; Inlet: 250° C., split ratio 100:1; constant flow: 1.0 mL/min; oven temperature profile: 40° C. (3 min), 10° C./min, 80° C. (0 min), 30° C./min, 250° C. (3 min); FID: 300° C., $H_2$ flow 30 mL/min, air flow 400 mL/min, make-up flow ($N_2$) 25 mL/min; internal standard: 1,1,1,3,5,5,5-heptamethyl trisiloxane):

| | Refrigerator (5° C.) Concentration (% w/w) | | | Freezer (−20° C.) Concentration (% w/w) | | |
|---|---|---|---|---|---|---|
| Stability Sample | 1-Nitrite | 2-Nitrite | Total | 1-Nitrite | 2-Nitrite | Total |
| Start High conc. | 3.75 | 2.94 | 6.69 | 3.75 | 2.94 | 6.69 |
| Start Medium conc. | 0.81 | 0.61 | 1.42 | 0.81 | 0.61 | 1.42 |
| Start Low conc. | 0.08 | 0.06 | 0.14 | 0.08 | 0.06 | 0.14 |
| 14 days High conc. | 3.72 | 2.91 | 6.63 | 3.76 | 2.89 | 6.65 |
| 10 days Medium conc. | 0.86 | 0.67 | 1.53 | 0.81 | 0.63 | 1.44 |
| 10 days Low conc. | 0.08 | 0.06 | 0.14 | 0.08 | 0.06 | 0.14 |
| 28 days High conc. | 3.67 | 2.90 | 6.57 | 3.72 | 2.93 | 6.65 |
| 27 days Medium conc. | 0.81 | 0.63 | 1.44 | 0.74 | 0.57 | 1.31 |
| 27 days Low conc. | 0.09 | 0.07 | 0.16 | 0.07 | 0.06 | 0.13 |
| 56 days High conc. | 3.47 | 2.69 | 6.16 | 3.55 | 2.74 | 6.29 |
| 64 days Medium conc. | 0.73 | 0.57 | 1.30 | 0.74 | 0.58 | 1.32 |
| 64 days Low conc. | 0.07 | 0.06 | 0.13 | 0.07 | 0.06 | 0.13 |
| 84 days High conc. | 3.33 | 2.59 | 5.92 | 3.50 | 2.71 | 6.21 |
| 84 days Medium conc. | 0.77 | 0.60 | 1.37 | 0.78 | 0.62 | 1.40 |
| 84 days Low conc. | 0.07 | 0.06 | 0.13 | 0.08 | 0.06 | 0.14 |

Note:
no build-up of pressure was observed for any of the samples.

Example 6—Solvent Free Preparation of 1-(nitrosooxy)-propan-2-ol, 2-(nitrosooxy)-propan-1-ol, and 1,2-bis(nitrosooxy)propane with Sodium Nitrite Water (30 mL) and sodium nitrite (19.01 g, 272.8 mmol) were added to a 100 mL three-necked round bottom flask, flushed with nitrogen and cooled down to 1° C. on a water bath cooled with an external cooler. 1,2-Propanediol (10 mL, 136.7 mmol) was added. Concentrated sulphuric acid (7 mL, 127.4 mmol) and water (20 mL) were pre-cooled to room temperature and added dropwise during one hour via a dropping funnel. During the addition, the water layer formed a thick slurry and a green second layer was formed. Before completion of acid addition (5 mL remaining) the flask was removed from the cooling bath and the green layer was decanted into a separation funnel and washed with 2×saturated aqueous $NaHCO_3$ solution. The green layer faded to yellow and after separation was dried over $Na_2SO_4$ and filtered through a syringe filter (Acrodisc® 13 mm, 0.45 μM SUPOR®) to yield 1.1 g mixture of approximately 0.25/0.1/1 of 1-(nitrosooxy)-propan-2-ol/2-(nitrosooxy)-propan-1-ol/1,2-bis(nitrosooxy)propane. No starting-material 1,2-propanediol could be detected within the limits of NMR sensitivity.

$^1$H-NMR, δ ppm: 5.81-5.76 (m, br, 1.0 H), 5.63 (br, 0.1 H), 4.93 (br, 2.08 H), 4.73-4.65 (br, m, 0.47 H), 4.14 (br, 0.19 H), 3.84-3.77 (br, m, 0.22 H), 1.49-1.48 (br, m, 3.21 H), 1.43 (br, 0.51 H), 1.28 (br, 0.72 H).

Example 7—Preparation of (2S)-1-(nitrosooxy)-propan-2-ol, (25)-2-(nitrosooxy)-propan-1-ol and (2S)-1,2-bis(nitrosooxy)propane (S)-1,2-propanediol (5 mL, 66.97 mmol), water (15 mL), dichloromethane (30 mL) and sodium nitrite (9.34 g, 134 mmol) were added to a 100 mL three-necked round bottom flask, flushed with nitrogen and cooled down to 1° C. on a water bath cooled with an external cooler. Concentrated sulphuric acid (3.5 mL, 63.69 mmol) and water (10 mL) were pre-cooled to room temperature and added dropwise via a syringe-pump during 1 h. After addition the mixture was stirred for additional 60 minutes. After separation of the two layers, the DCM layer was diluted with additional DCM (15 mL) and washed with sat. aq. $NaHCO_3$ (15 mL), followed by brine (15 mL), then dried over $Na_2SO_4$, filtered over a sintered glass filter and reduced in vacuo. The residue was taken up again in 30 mL DCM, washed with 1.4% w/w aq. bicarbonate solution, then dried over $Na_2SO_4$, filtered over a sintered glass filter and reduced in vacuo to yield 1 g of product mixture. The mixture of consisted of (2S)-1,2-propanediol (3%), (2S)-1-(nitrosooxy)-propan-2-ol (23%), (2S)-2-(nitrosooxy)-propan-1-ol (14%) and (2S)-1,2-bis(nitrosooxy)propane (60%) based on NMR.

$^1$H-NMR, δ ppm: 5.83-5.74 (m, 1.0 H), 5.66-5.57 (br, 0.22 H), 4.99-4.85 (br, 1.98 H), 4.76-4.59 (br, 0.77 H), 4.17-4.07 (br, 0.38 H), 3.86-3.73 (br, 0.40 H), 1.8-1.6 (br, 0.97 H), 1.48 (d, J=6.7 Hz, 3.12 H), 1.40 (d, J=6.6 Hz, 0.63 H), 1.28 (d, J=6.5 Hz, 1.15 H).

Example 8—Preparation of (2R)-1-(nitrosooxy)-propan-2-ol, (2R)-2-(nitrosooxy)-propan-1-ol and (2R)-1,2-bis(nitrosooxy)propane (R)-1,2-propanediol (5 mL, 66.97 mmol), water (15 mL), dichloromethane (30 mL) and sodium nitrite (9.34 g, 134 mmol) were added to a 100 mL three-necked round bottom flask, flushed with nitrogen and cooled down to 1° C. on a water bath cooled with an external cooler. Concentrated sulphuric acid (3.5 mL, 63.69 mmol) and water (10 mL) were pre-cooled to room temperature and added dropwise via a syringe-pump during 1 h. After addition the mixture was stirred for additional 55 minutes. After separation of the two layers, the DCM layer was diluted with additional DCM (10 mL) and washed with saturated aqueous $NaHCO_3$ (20 mL), then dried over $Na_2SO_4$, filtered over a sintered glass filter and reduced in vacuo. The mixture of consisted of (2R)-1,2-propanediol (17%), (2R)-1-(nitrosooxy)-propan-2-ol (16%), (2R)-2-(nitrosooxy)-propan-1-ol (7%) and (2R)-1,2-bis(nitrosooxy)propane (59%) based on NMR.

$^1$H-NMR, δ ppm: 5.83-5.74 (m, 1.0 H), 5.66-5.57 (br, 0.12 H), 4.99-4.85 (br, 2.10 H), 4.76-4.59 (br, 0.53 H), 4.17-4.07 (br, 0.24 H), 3.86-3.73 (br, 0.28 H), 2.4-2.1 (br, 0.38 H), 1.48 (d, J=6.8 Hz, 3.20 H), 1.40 (br, 0.56 H), 1.28 (br(d), 0.88 H).

Example 9—Preparation of 1-(nitrosom)propan-3-ol and 1,3-bis(nitrosooxy)propane 1,3-propanediol (2.5 g, 32.86 mmol), water (7 mL), dichloromethane (15 mL) and sodium nitrite (4.53 g, 65.7 mmol) were added to a 100 mL round bottom flask, flushed with nitrogen and cooled down to 0° C. for 15 min on a water bath cooled with an external cooler. Concentrated sulphuric acid (1.7 mL, 31.2 mmol) and water (5 mL) were pre-cooled to room temperature and added dropwise for 5 minutes. After addition the mixture was stirred for additional 60 minutes at 0° C. The two layers was then separated, and the organic phase was diluted with additional DCM (10 mL), washed with saturated aqueous $NaHCO_3$ (2×25 mL), dried over $MgSO_4$, filtered over a sintered glass filter. Finally, 1,3-propanediol (16.4 g 216 mmol) was added to the organic phase followed by removal of DCM in vacuo. Based on NMR the mixture (18.1 g) contained 1,3-propandiol (86.9 wt. %), 1-(nitrosooxy)-propan-3-ol (11.8 wt. %), and 1,3-bis(nitrosooxy)propane (1.3 wt. %).

1H-NMR, δ 4.76-4.88 (m, 2H), 3.83 (t, J=5.7 Hz, 2H), 3.73 (t, J=6.1 Hz, 2H), 2.79 (s, 1H), 2.18 (quintet, J=6.3 Hz, 2H), 1.99 (quintet, J=6.2 Hz, 2H), 1.80 (quintet, J=5.7 Hz, 2H).

Example 10—Scaled Up Process for the Preparation of 1-(nitrosooxy)-propan-2-ol, 2-(nitrosooxy)-propan-1-ol and 1,2-bis(nitrosooxy)propane with sodium nitrite 10.1 Chemicals Used Starting materials were purchased from the list of suppliers in the table below. Unless otherwise noted the chemicals were used as received without further purification.

| List of used chemicals and solvents Chemical/Solvent | Grade | Supplier |
|---|---|---|
| 1,2-Propanediol | EMPROVE ® ESSENTIAL Ph. Eur. or BP or USP, ≥99% | Merck |
| Sodium nitrite | Conforms to current ACS, USP or Ph. Eur., ≥97% | VWR, Acros |
| Sulfuric acid | ≥95.0, Conforms to current ACS, USP or Ph. Eur. | VWR, Acros |
| TBME | Conforms to current ACS, USP or Ph. Eur., ≥99% | VWR, Acros |
| Sodium bicarbonate | Conforms to current ACS, USP or Ph. Eur. | VWR, Acros |
| Magnesium sulfate | USP, dried | VWR, Acros |
| Argon | 4.8 or higher | Linde AG, Westfalen AG |

10.2 General Procedure for the Synthesis of PDNO Using DCM as Solvent (Origin Process)

A round bottom flask was equipped with a stirrer and dropping funnel. Water (3.0 veq.) was added and sodium nitrite (2.0 equiv.) was charged to the flask. The solution was cooled (0° C.) and PD (1.0 equiv.) and DCM (6 rel. vol.) were also added. During further cooling, a sulfuric acid solution (1.0 eq. $H_2SO_4$, 2.0 rel. vol. water) was prepared. The sulfuric acid solution was further added dropwise to the reaction mixture while keeping the reaction mixture between 0° C. and 5° C. After complete addition of the acid, the solution was further stirred for 1 h to complete reaction.

Then, the reaction was quenched with saturated $NaHCO_3$ solution (6.0 rel. vol.). The phases were separated, and the organic layer was further washed with $NaHCO_3$ solution (6.0 rel. vol.). The organic phase was dried over $MgSO_4$, filtered, diluted with PD, and concentrated under reduced pressure using a rotary evaporator (water bath temperature 40° C.).

The product was obtained as a slightly yellowish liquid.

10.3 General Synthesis of PDNO Using TBME as Solvent

A round bottom flask was equipped with stirrer and dropping funnel. Argon was flushed through for several minutes. A diluted sulfuric acid solution (1.0 eq. $H_2SO_4$, 2.0 rel. vol. water) was prepared in advanced and precooled (−30° C.). Water was added to the flask (3.0 rel. vol.). Sodium nitrite (2.0 equiv.) was added into the water. TBME (7.5 rel. vol.) was added. Propanediol (1.0 equiv.) was added and the reaction mixture was cooled (−20° C.) flushing constantly with argon. The reaction mixture was stirred well while adding dropwise the precooled sulfuric acid. The reaction temperature was monitored during the entire addition of the acid. After addition, the reaction mixture was further stirred (30-60 min) at cold temperature (−20° C.). Afterwards, the reaction mixture was allowed to warm up (−5° C.). The reaction was stopped by quenching with saturated $NaHCO_3$ solution (6.0 rel. vol.). The phases were separated. The organic layer was further washed with saturated $NaHCO_3$ solution until a pH value of 7-8 was obtained. The organic phase was then dried over $MgSO_4$. The crude PDNO solution was diluted with PD (3 rel. vol.) and further concentrated under reduced pressure at ambient temperature (25° C.).

The crude PDNO solution was further purified using a vertical tube evaporation apparatus.

PDNO was obtained as a slightly yellowish liquid.

10.4 Detailed Synthesis of PDNO Using TBME as Solvent

The process was designed to produce approx. 7.5 L of 7% PDNO solution with one synthesis (one "run"). The synthesis was performed several times, to give the desired batch size. GC analysis was used each single run for purity determination. The runs which are within the specifications for the organic related compounds can be blended together to yield one batch. The entire crude PDNO batch was then purified. After purification, the strong PDNO solution was then further diluted with PD to yield the desired concentration (usually 7% PDNO solution).

A suitable double wall reactor (60 L) was equipped with specific "cup-stirrer", dropping funnel and attachment for argon. The reactor was flushed for 5 min to 10 min with a constant argon stream. Water (3.0 L) was added to the reactor. Sodium nitrite (2.0 equiv., 1886 g) was added through the reactor. The reaction was further stirred until all of the salt was dissolved. 1,2-propanediol (1.0 equiv., 1040 g, 1 L) was added, followed by tert-butylmethyl ether (7.5 rel. vol., 7.5 L). The reaction mixture was then cooled by continuous stirring and argon flow at an inner reaction temperature of −20° C. Meanwhile sulfuric acid (1.0 equiv., 1340 g, 728 mL) was diluted with water (2.0 L) and cooled at −30° C. After reaching an inner reaction temperature of −20° C., the diluted acid was added dropwise to the reaction mixture while vigorous stirring.

The stirring speed was varied during the addition of the acid. Starting with approx. 350 rpm to a slower stirring speed by the end of the reaction (approx. 180 rpm.). This variation of the stirring speed is due the two-phase reaction system and the slowly precipitation of sodium sulfate by further progress of the reaction (due to the addition of more and more sulfuric acid).

During the entire addition of the sulfuric acid, the reaction temperature was monitored. The temperature should ideally be in range of (−20±3) ° C. In addition, the reaction was stirred for 30-60 min at (−20±3) ° C.

The reaction was allowed to warm up to −5° C. to 0° C. The reaction was stopped by the addition of saturated $NaHCO_3$ solution (6.0 rel. vol 6.0 L) followed by the addition of water (10 L). The phases were separated and the organic layer was transferred into a separate double wall reactor and chilled at 0° C. to −5° C. The organic layer was washed several times (approx. 2-3 times) with saturated $NaHCO_3$ solution (4.0 rel. vol., 4.0 L). The pH value of the water phase was monitored after each washing step. The pH value was about 7-8. The water phases were discarded. The organic layer was dried over $MgSO_4$ and filtered over a Whatman filter paper.

The crude PDNO (solution in TBME) was diluted by the addition of further PD (3.0 rel. vol., 3.0 L). This crude PDNO was transferred to a rotary evaporator and concentrated under reduced pressure. The water bath temperature during the evaporation was maintained at a maximum temperature of 25° C. The evaporation of the main amount of TBME was removed in a time range between 1.5 h and 2.0 h.

The evaporation of the organic solvents could then be continued at a water bath temperature at (0±2) ° C. for several hours using a high vacuum pump (during the development the PDNO purity was monitored at these conditions, and over a period of 6 h the product purity was not affected).

10.5 Further Purification of the Crude PDNO Solution

The final purification of the PDNO solution was done by vertical tube evaporation. The PDNO solution was distilled under high vacuum with a continuous thin steam of PDNO at 0° C. The storing tank for the "crude" PDNO solution was chilled at 0° C. The entire distillation was performed at 0° C. The storage tank for the "purified" PDNO was also chilled at −10° C. to 0° C. After each run of the evaporation of the entire batch PDNO, the residual organic solvent (TBME) can be checked via GC. This evaporation was continued until the desired limit for the residual solvents was achieved. In the case of PDNO the limit for the residual solvent is 1000 ppm.

10.6 Preparation of the Final Dilution

After purification, PDNO was further diluted to reach the favoured concentration. The first step was to filter the PDNO solution into a clean glass bottle via Whatman filter. In addition, the assay of the PDNO solution was determined via q-NMR. The amount of PD for dilution can be calculated. The PD was filtered first over a Whatman filter. The final dilution can be done at ambient temperatures. The calculated amount of PD was added to the PDNO solution (or the other way around). The resulting mixture was shaken for several minutes to obtain a homogeneous solution. The final PDNO solution was filled into the product bottles.

PDNO (7.5 kg; 7 wt. % solution) was yielded as a slightly yellowish liquid.

Example 11—First Set of In Vivo Studies 11.1 Material and Methods

Prior to experimentation, ethical approval was received from Linkoping's regional animal ethics committee (Linköping, Sweden; approval number 953). Anaesthetic management, surgical instrumentation and methods for measurements were recently described (Dogan et al. 2018, Sadeghi et al. 2018, Stene Hurtsén 2020). In brief, 13 male and female pigs (a crossbreed between Swedish country breed, Hampshire and Yorkshire; 3-4 months old; 24-26 kg) were premedicated with azaperone at the farm and transported to the laboratory.

At the laboratory, anaesthesia was induced with a mixture of tiletamine, zolazepam and azaperone (intramuscular injection). Propofol was given in a peripheral venous catheter in an ear vein, if needed. Bolus doses of atropine and cefuroxime were administered intravenously. The animals were endotracheally intubated and mechanically ventilated (5 cm $H_2O$ in positive end-expiratory pressure, minute ventilation was adjusted to normoventilation). General anaesthesia was maintained with propofol and remifentanil via continuous intravenous infusions, and additional bolus doses were given if needed. Ringer's acetate and glucose solutions were continuously administered intravenously to substitute for fluid loss. Heparin was given as an intravenous bolus dose after the surgical instrumentation. After the experiments, the animals were killed in general anaesthesia with a propofol injection followed by a rapid intravenous injection of potassium chloride (40 mmol), and asystolia was confirmed.

The animals were instrumented with an arterial catheter in the right carotid artery for measurement of systemic arterial blood pressure and heart rate. A sheath was placed in the right external jugular vein for introduction of a pulmonary-arterial catheter. This catheter was used for continuous measurement of pulmonary arterial blood pressure, semi-continuous cardiac output and intermittent pulmonary wedge pressure. A central venous catheter was inserted in the left external jugular vein for drug and fluid administration. All fluid and drug administrations were done by motorised syringe or drip pumps. The urinary bladder was catheterized. Respiratory gases including the fraction of nitric oxide, pressures and volumes were measured at the endotracheal tube. Respiratory and hemodynamic variables were measured by a Datex AS/3 (Helsinki, Finland) and data were collected by a computerised system (MP100 or MP150/Acknowledge 3.9.1, BIOPAC systems, Goleta, CA, USA). After surgical instrumentation, a 1 h intervention-free period followed.

Data were presented as means and standard error of the means where applicable.

11.2 Experimental Protocol

After collecting baseline data, several administration routes of PDNO (i.e. the product that comprises one of, or a mixture of, 1-(nitrosooxy)-propan-2-ol, 2-(nitrosooxy)-propan-1-ol and 1,2-bis(nitrosooxy)propane prepared as outlined above) were investigated in the same animal with stabilisation in between.

11.2.1 Experiments at Normal Pulmonary Vascular Resistance

Intravenous infusions of PDNO into a carrier flow of a solution of sodium bicarbonate (14 mg ml-1; pH approximately 8; infusion rate 9 times of the PDNO infusion rate) in increasing doses (5, 10, 20, 40 and 80 nmol $kg^{-1}$ $min^{-1}$) for 30 min at each dose were done. Subcutaneous (in the neck) and intramuscular (gluteal muscles) infusion in increasing dose (subcutaneous: 100, 200, 400, 800 and 1600 nmol $kg^{-1}$ $min^{-1}$; intramuscular: 50, 100, 200, 400 and 800 nmol $kg^{-1}$ $min^{-1}$) for 5 min followed by 25 min observation for each dose were done. Intranasal bolus application of PDNO in two doses (500 and 2500 nmol $kg^{-1}$) were done in one nostril.

11.2.2 Experiments at Increased Pulmonary Vascular Resistance

Pulmonary arterial pressure was increased to approximately 35 mmHg by a continuous intravenous infusion of U46619 (Cayman Chemical, MI, USA). Thereafter, intravenous and subcutaneous infusions of PDNO in increasing doses (intravenous: 5, 15 and 45 nmol $kg^{-1}$ $min^{-1}$ for 15 min at each dose; subcutaneous: 200, 600 and 1800 nmol $kg^{-1}$ $min^{-1}$ for 5 min followed by 10 min observation at each dose).

In an additional experiment, pulmonary arterial pressure was increased by permissive hypercapnia (end-tidal carbon dioxide fraction of approximately 8%). Thereafter, a few ml of PDNO (203 mM) were applied in a commercially available electronic cigarette (eGo AIO, Joyetech). Gas from the electronic cigarette was sampled in a 50 ml syringe and injected into the inspiratory limp of the ventilator circuit in one single breath, thus administering PDNO via inhalation. It was repeated after stabilisation and control inhalations were made with room air.

11.3 Results

Figure 2:
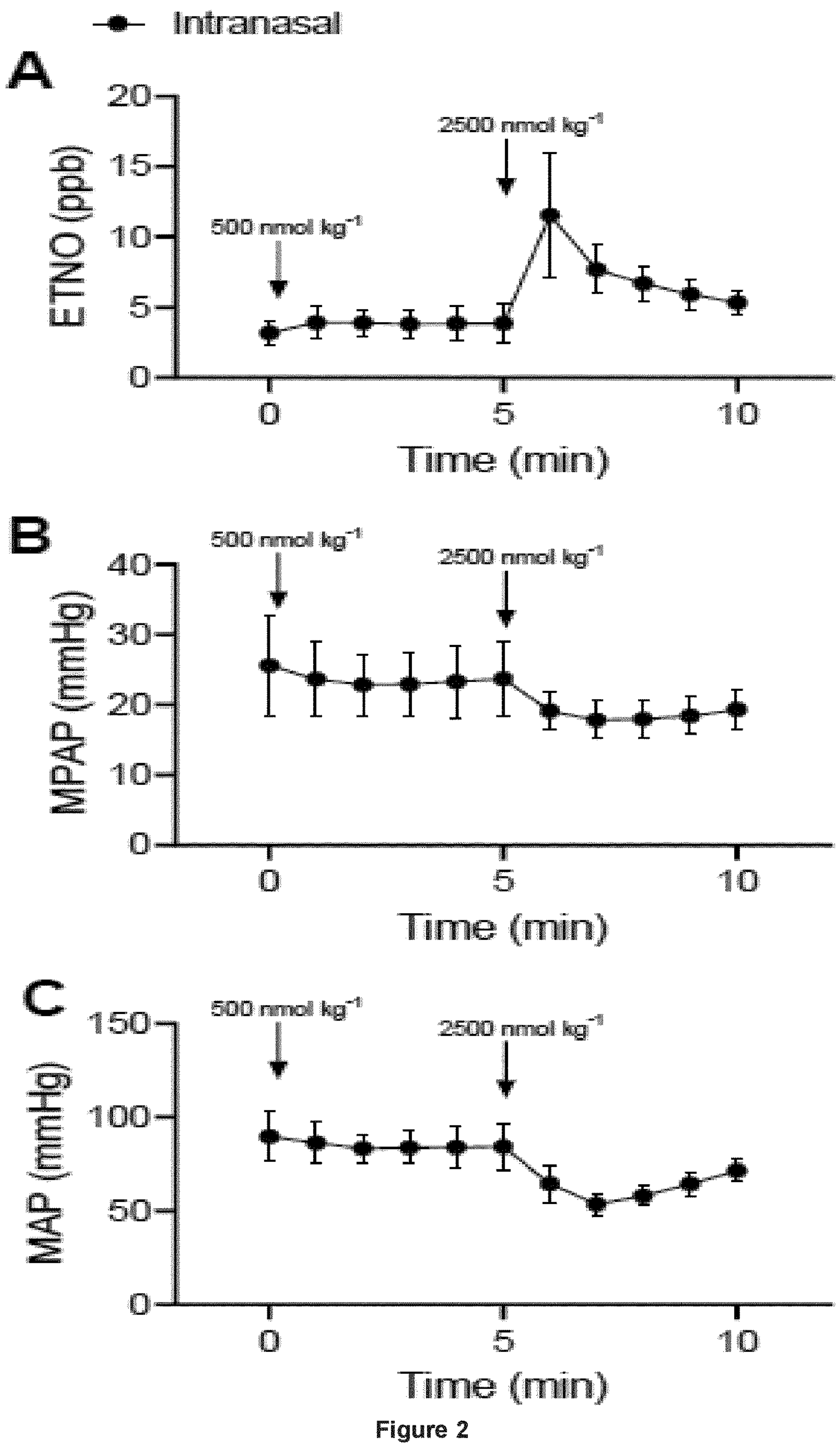
FIG. 2 details the effects of intranasal PDNO administration (n=6) on exhaled nitric oxide (ETNO, panel A), mean pulmonary arterial pressure (MPAP, panel B) and mean arterial pressure (MAP, panel C) in anesthetised naïve pigs. Data are means with standard error of the mean.
Figure 3A:
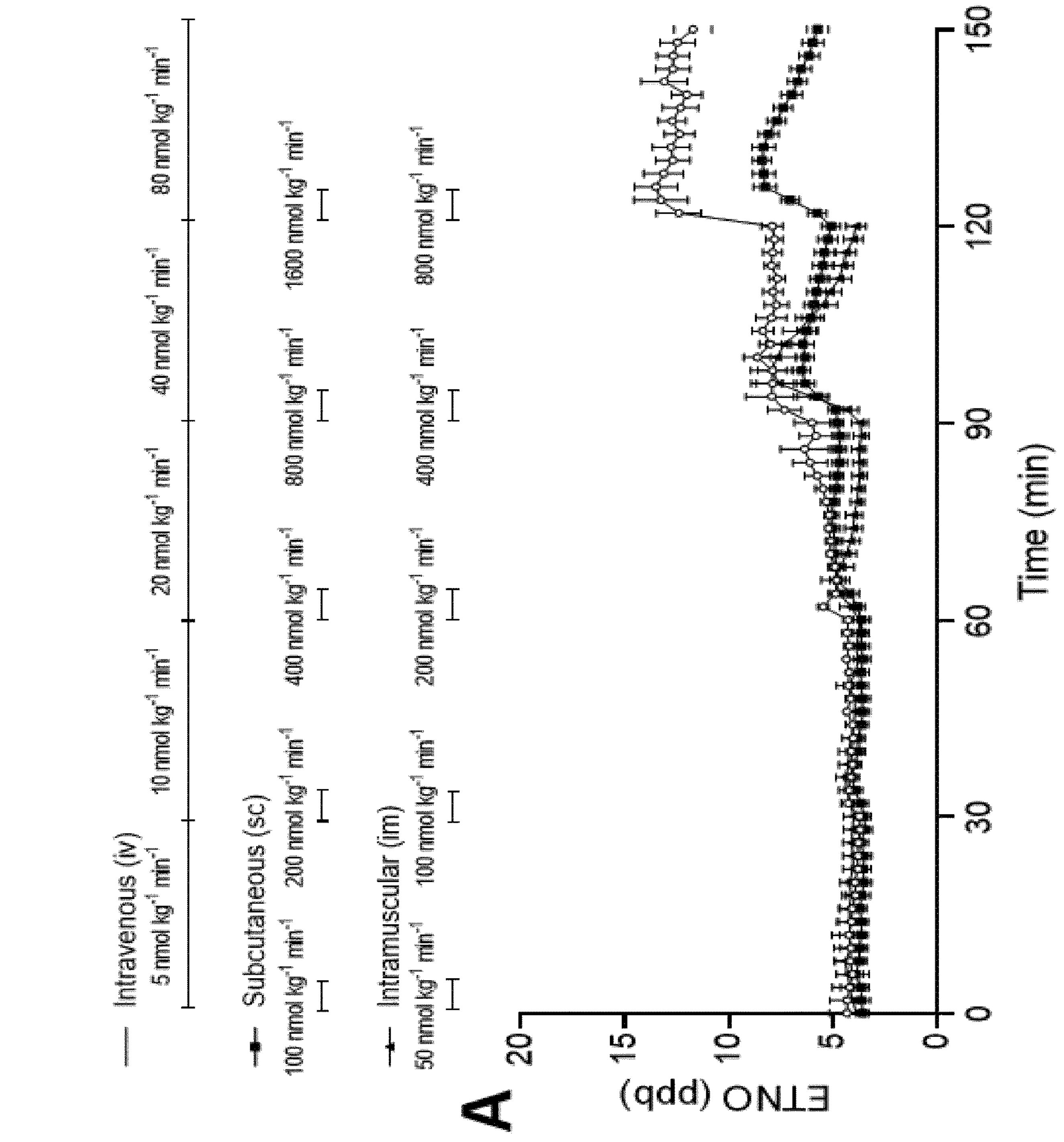
FIG. 3 details the effects of PDNO on end-tidal nitric oxide (ETNO, panel A) and mean arterial pressure (MAP, panel B) administered intravenously (5-80 nmol kg-1 min-1 for 30 min each, n=6), subcutaneously (100-1600 nmol kg-1 min-1 for 5 min each, n=6) and intramuscularly (50-800 nmol kg-1 min-1 for 5 min each, n=4-6) in anesthetised naïve pigs having normal pulmonary vascular resistance. Data are means with standard error of the mean. The intravenous data is included herein as a reference example.
Figure 3B:
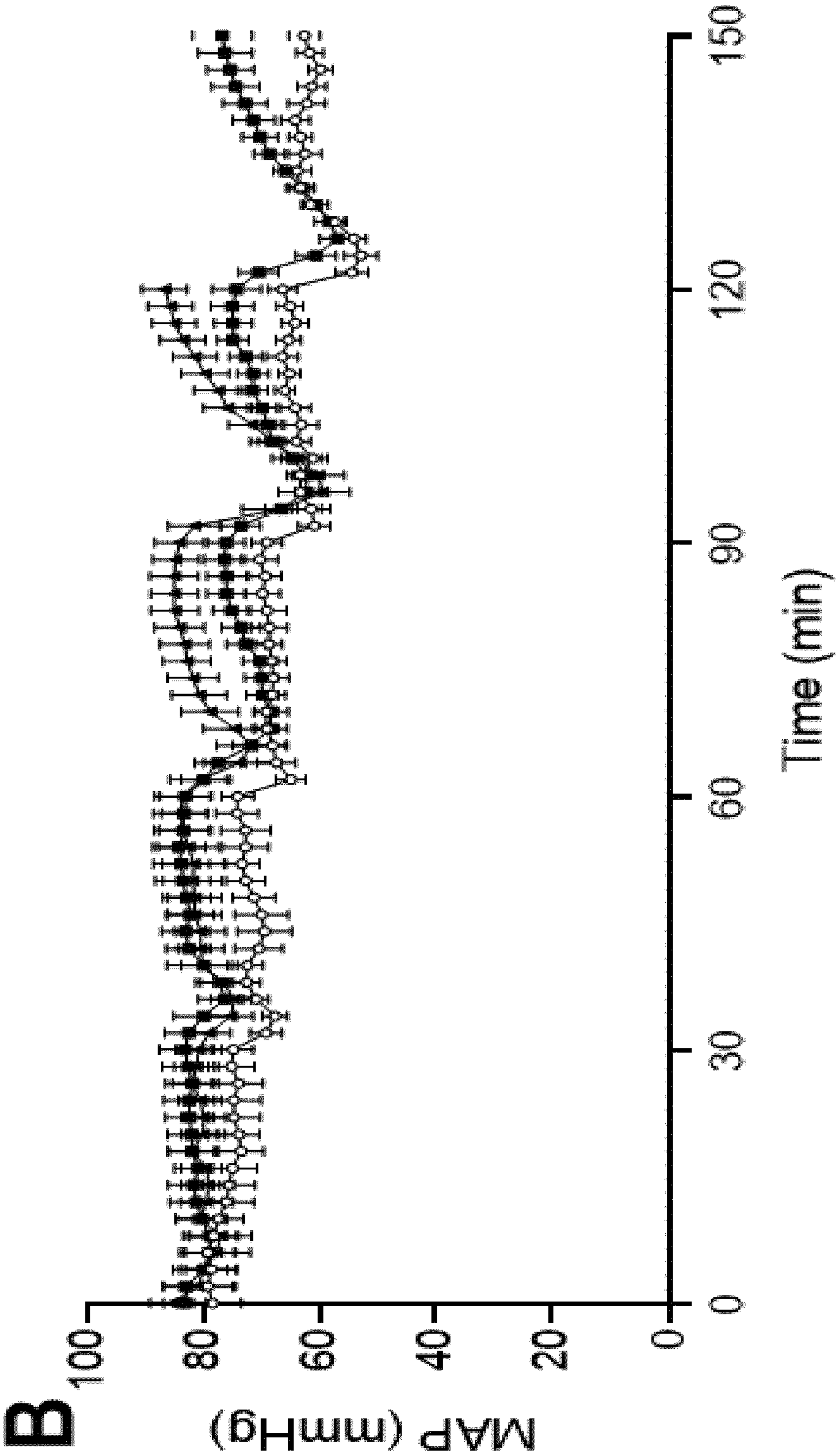
Figure 4A:
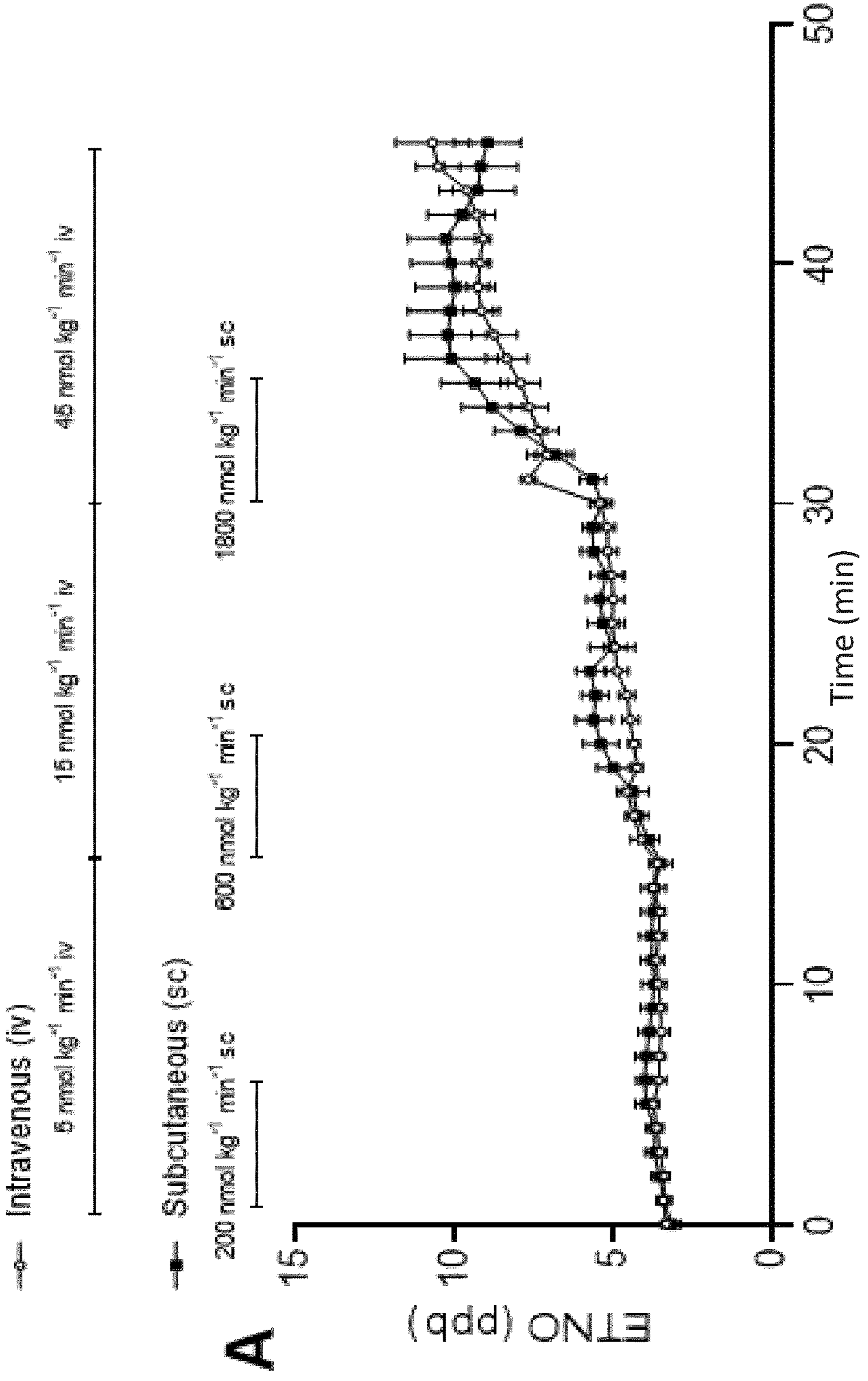
FIG. 4 details the effects of PDNO on end-tidal nitric oxide (ETNO, panel A), mean pulmonary arterial pressure (MPAP, panel B) and mean arterial pressure (MAP, panel C) administered either intravenously (5, 15 and 45 nmol $kg_{-1}$ $min_{-1}$ for 15 min each, n=4) or subcutaneously (200, 600 and 1800 nmol $kg_{-1}$ $min_{-1}$ for 5 min each, n=5) in anesthetised pigs with aPH (induced by a continuous intravenous infusion of U46619). Data are means with standard error of the mean. The intravenous data is included herein as a reference example.
Figure 4B:
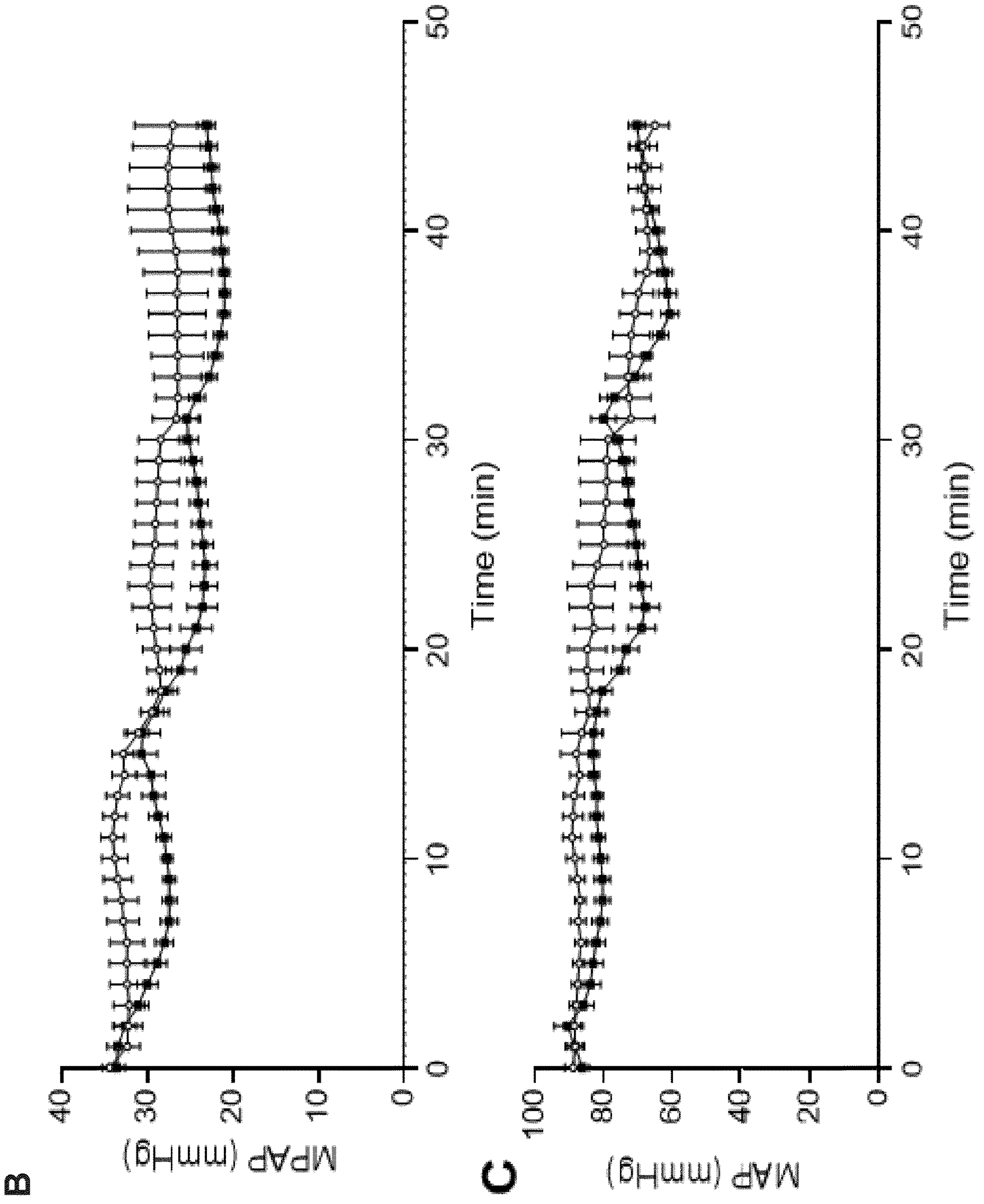
Figure 5:
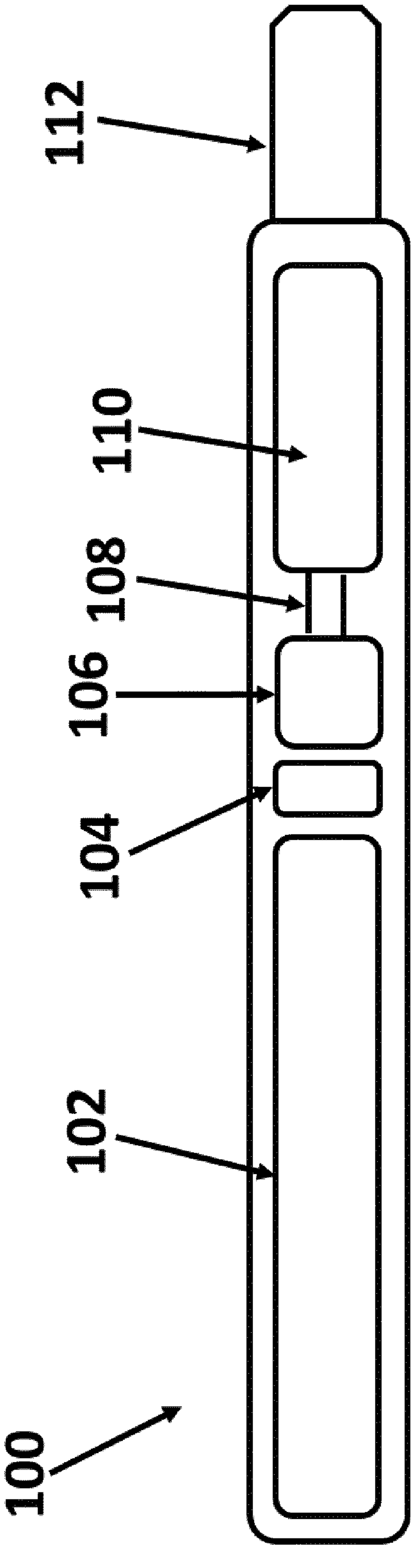
FIG. 5 depicts a typical device for use in the third aspect of the invention for administering the substantially non-aqueous composition to a patient via inhalation. The device (100) comprises a battery (102), a microprocessor (104), a heating element (106), a wick (108), a mouthpiece (112) and a removable cartridge reservoir (110) for containing the substantially non-aqueous composition.
Figure 6:
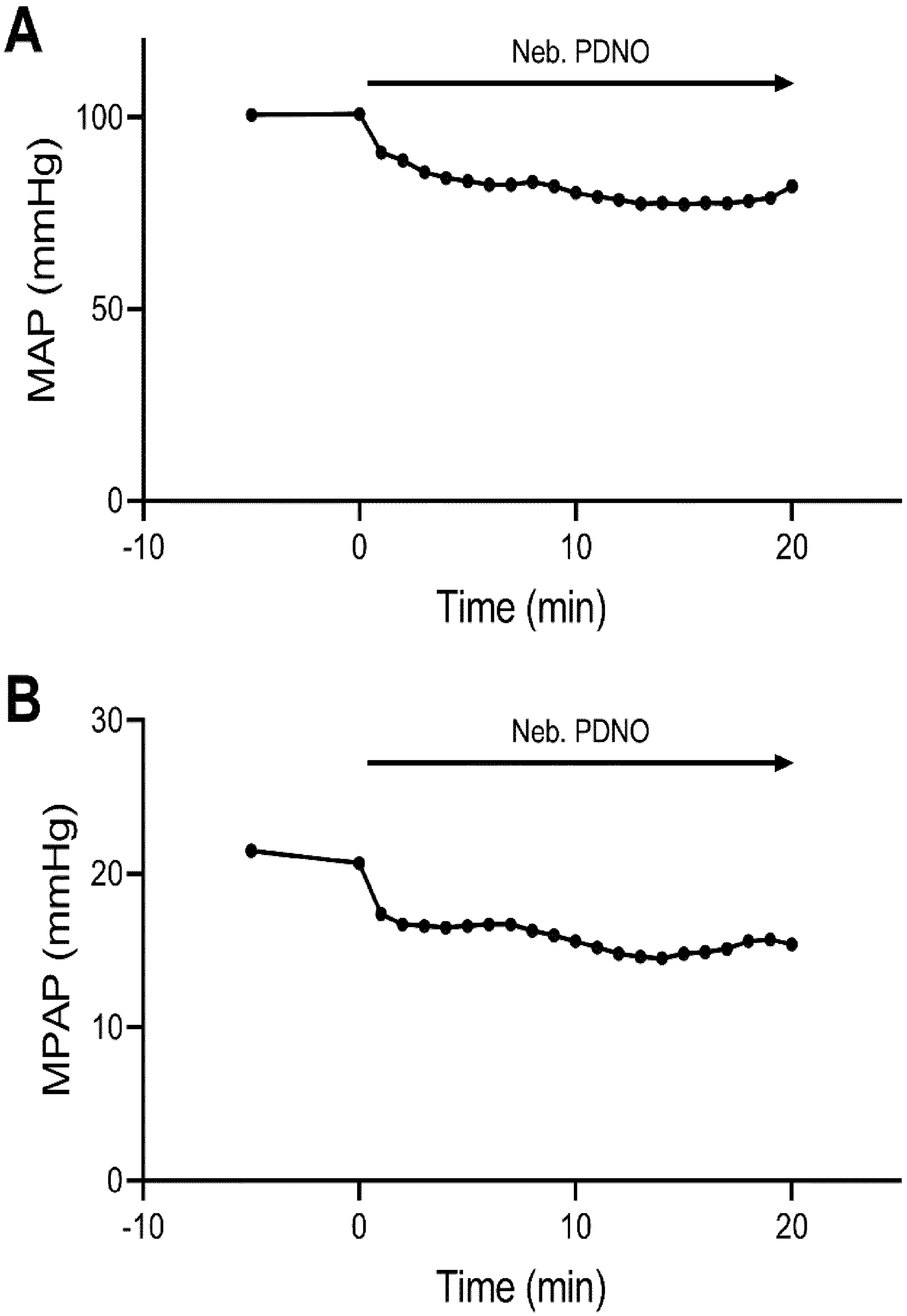
FIG. 6 depicts the mean systemic and pulmonary arterial pressure (MAP and MPAP, respectively) in an anesthetised and mechanically ventilated pig where pulmonary arterial pressure was increased by permissive hypercapnia (end-tidal carbon dioxide fraction of approximately 8-9%). One-part PDNO (203 mM) was dissolved in four parts of sodium bicarbonate (50 mg-1) and nebulised with an ordinary intensive care unit nebuliser for 5-20 min.
Figure 7:
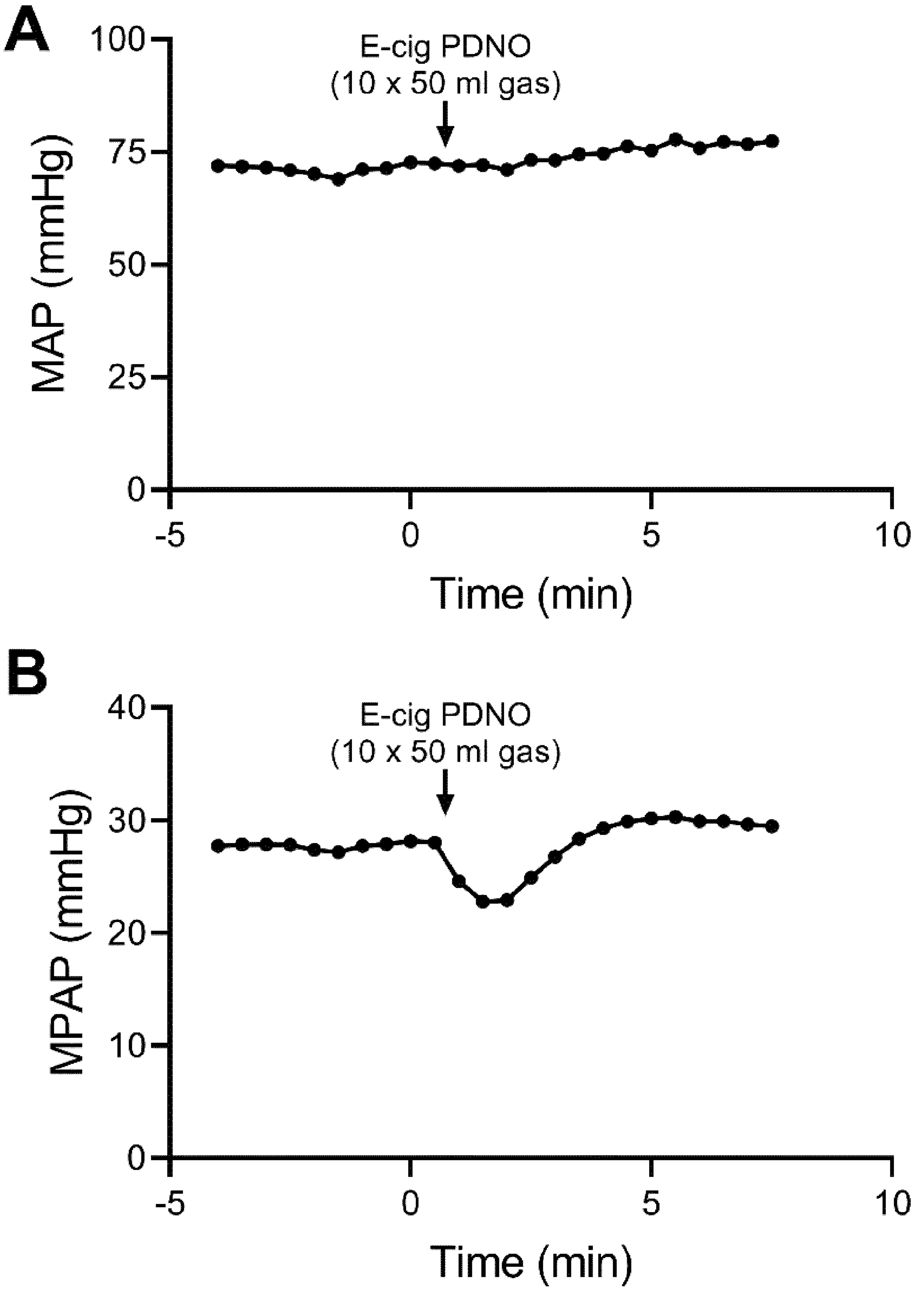
FIG. 7 depicts mean systemic and pulmonary arterial pressure (MAP and MPAP, respectively) in an anesthetised and mechanically ventilated pig where pulmonary arterial pressure was increased by permissive hypercapnia (end-tidal carbon dioxide fraction of approximately 8-9%). A few ml of PDNO (203 mM) were applied in a commercially available electronic cigarette (eGo AIO, Joyetech). Gas from the electronic cigarette was sampled in a 50 ml syringe and injected into the inspiratory limp of the ventilator circuit. This procedure was repeated for approximately 10 times with very short interval.
Figure 8:
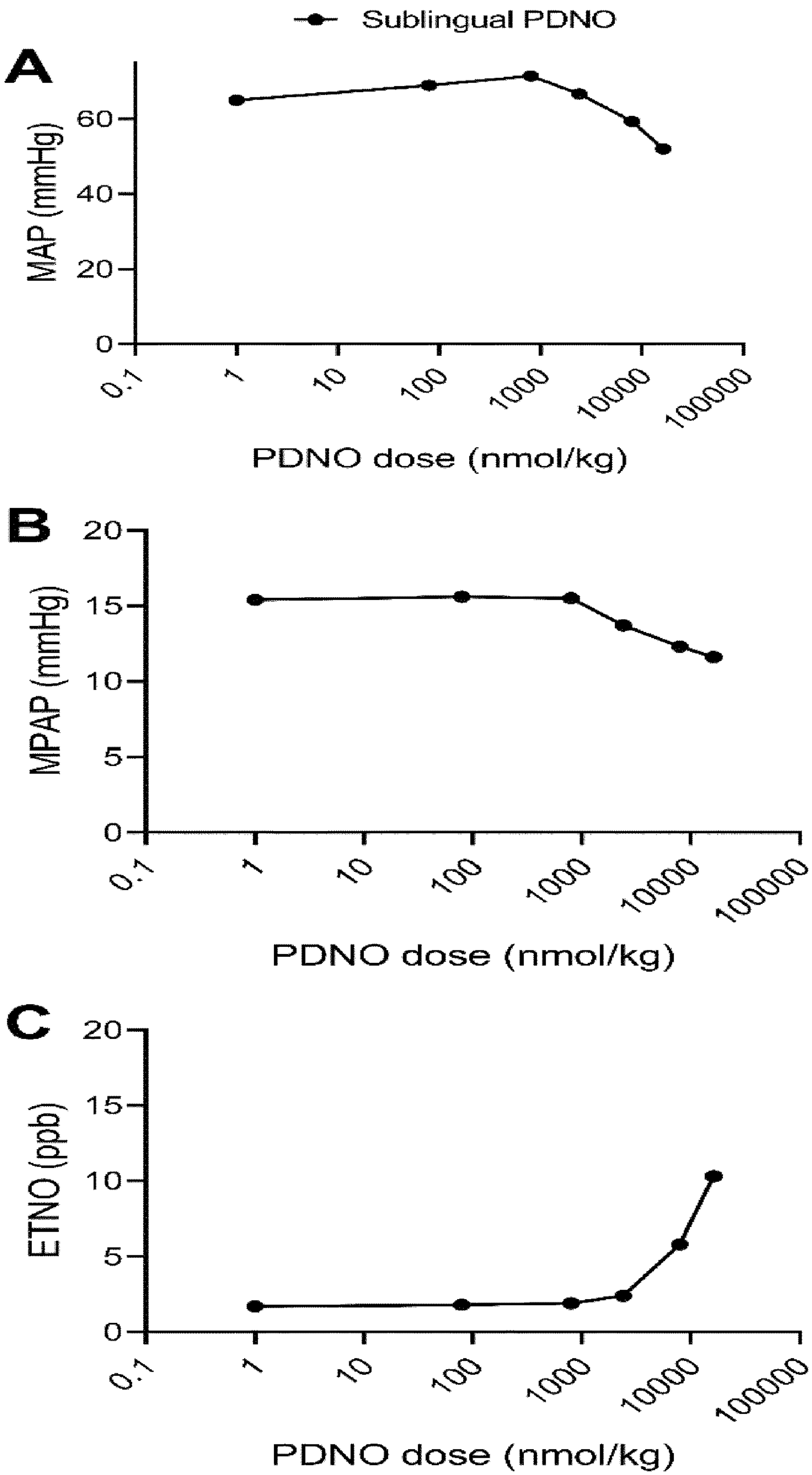
FIG. 8 depicts mean systemic arterial pressure (MAP, panel A), mean pulmonary arterial pressure (MPAP, panel B) and end-tidal concentration of nitric oxide (ETNO, panel C) in an anesthetised pig subjected to increasing doses of PDNO applied sublingually by a small compress soaked with 2 ml PDNO in increasing concentrations (1 mM-203 mM) for 15 min.
Figure 9:
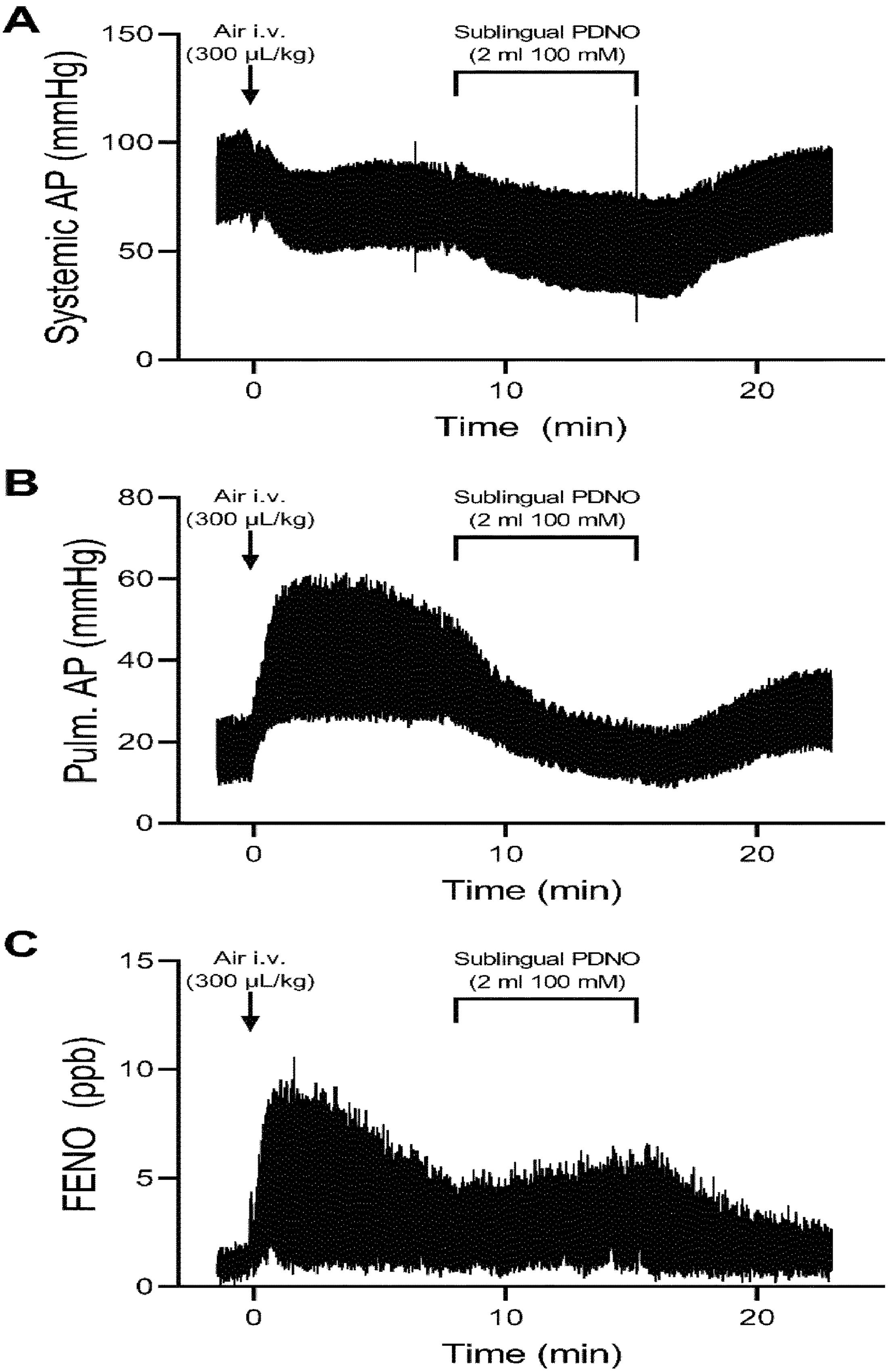
FIG. 9 depicts systemic and pulmonary arterial pressure (AP, panel A and B), and end-tidal concentration of nitric oxide (FENNO, panel C) in an anesthetised pig subjected air pulmonary embolization by a fast injection of 300 microl/kg air intravenously and sublingual PDNO by a small compress soaked with 2 ml PDNO in (100 mM).
Figure 10:
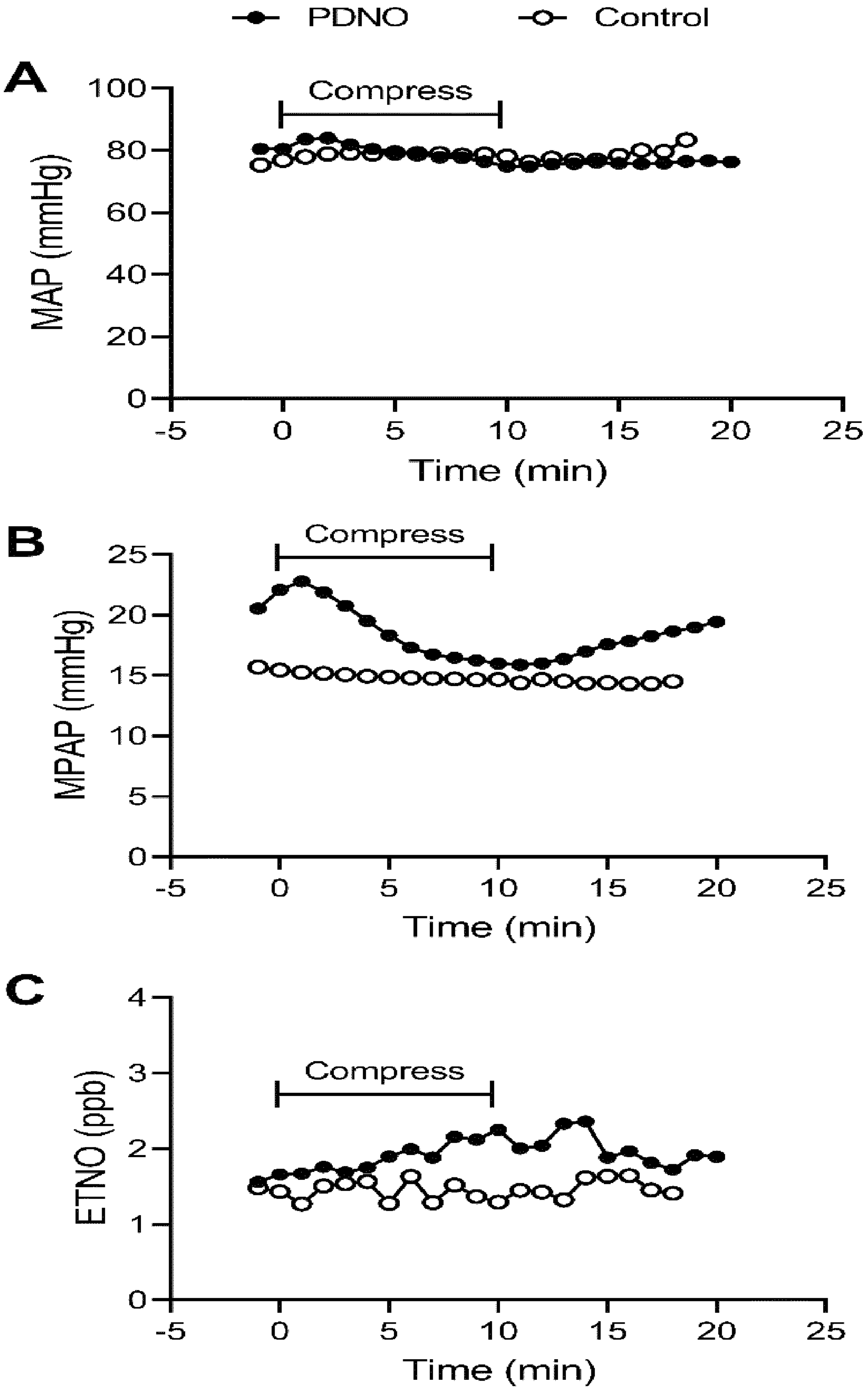
FIG. 10 depicts mean systemic arterial pressure (MAP, panel A), mean pulmonary arterial pressure (MPAP, panel B) and end-tidal concentration of nitric oxide (ETNO, panel C) in an anesthetised pig (25 kg) subjected to dermal application of 3 small compresses soaked with 2 ml PDNO (203 mM) or 3 compresses without PDNO (control). The skin was pretreated with transdermal catalyser menthone.
Figure 11:
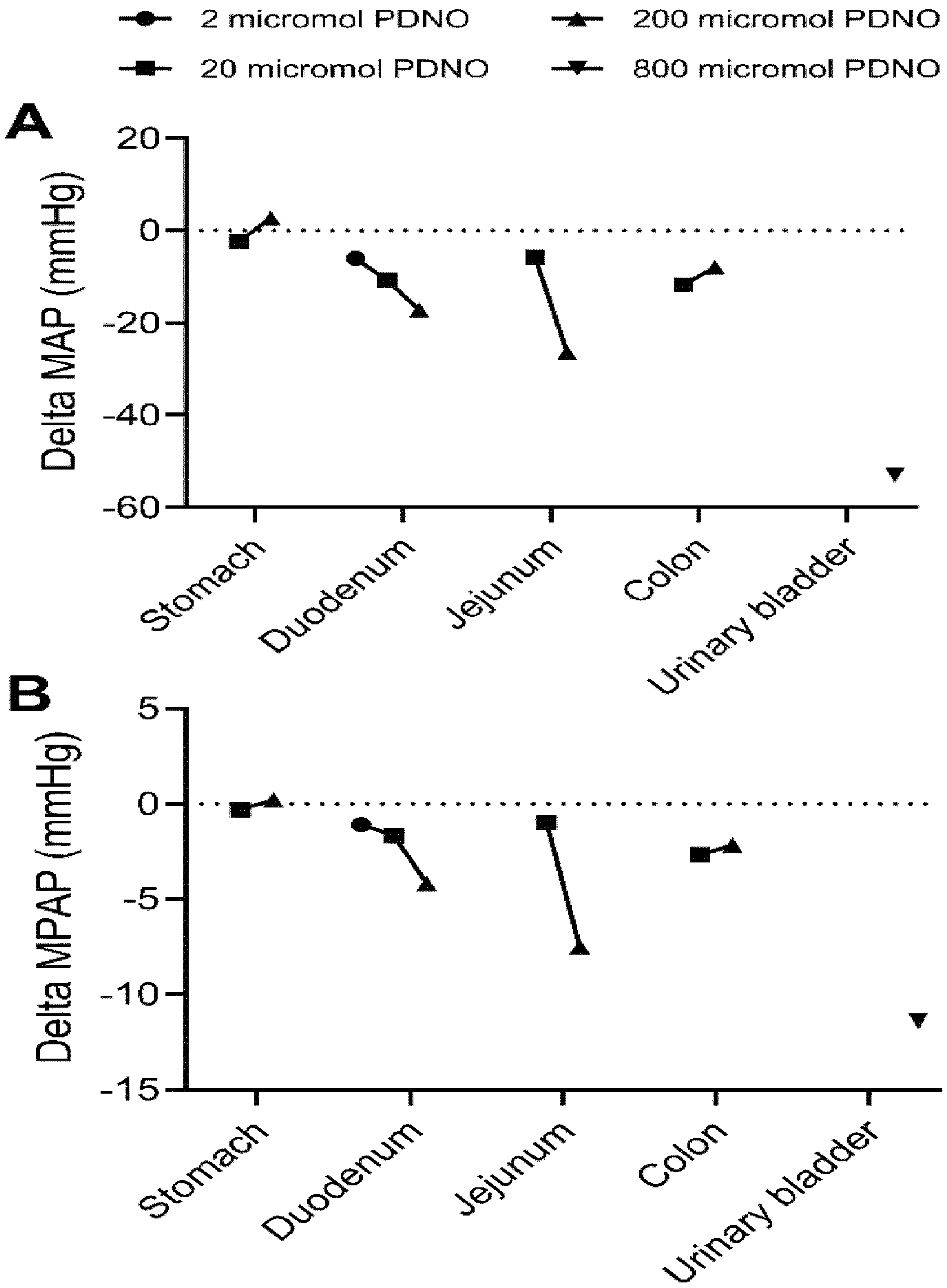
FIG. 11 depicts change in mean systemic arterial pressure (Delta MAP, panel A) and mean pulmonary arterial pressure (MPAP, panel B) in an anesthetised pig subjected to injection of PDNO (2-4 ml of 1 mM, 10 mM, 100 mM and 200 mM) via catheter in various body cavities.

At normal vascular resistance, intravenous, subcutaneous, intramuscular and intranasal administration of PDNO caused dose-dependent increments of end-tidal fraction of nitric oxide and lowering of systemic mean arterial pressure (FIG. 2-3). At increased pulmonary vascular resistance, intravenous and subcutaneous infusions of PDNO caused dose-dependent increments of end-tidal fraction of nitric oxide and lowering of systemic and pulmonary mean arterial pressure (FIG. 4). Inhalation of PDNO caused small decrements of mean pulmonary arterial pressure whereas mean systemic arterial pressure was unchanged (FIG. 4).

Example 12—Second Set of In Vivo Studies 12.1 Material and Methods

Prior to experimentation, ethical approval was received from Linkoping's regional animal ethics committee (Linkoping, Sweden; approval number 953). Anaesthetic management, surgical instrumentation and methods for measurements were recently described (Dogan et al. 2018, Sadeghi et al. 2018, Stene Hurtsén 2020). In brief, 11 male and female pigs (a crossbreed between Swedish country breed, Hampshire and Yorkshire; 3-4 months old; 20-35 kg) were premedicated with azaperone at the farm and transported to the laboratory. At the laboratory, anaesthesia was induced with a mixture of tiletamine, zolazepam and azaperone (intramuscular injection). Propofol was given in a peripheral venous catheter in an ear vein, if needed. Bolus doses of atropine and cefuroxime were administered intravenously. The animals were endotracheally intubated and mechanically ventilated (5 cm $H_2O$ in positive end-expiratory pressure, minute ventilation was adjusted to normoventilation). General anaesthesia was maintained with propofol and remifentanil via continuous intravenous infusions, and additional bolus doses were given if needed. Ringer's acetate and glucose solutions were continuously administered intravenously to substitute for fluid loss. Heparin was given as an intravenous bolus dose after the surgical instrumentation. After the experiments, the animals were killed in general anaesthesia with a propofol injection followed by a rapid intravenous injection of potassium chloride (40 mmol), and asystolia was confirmed.

The animals were instrumented with an arterial catheter in the right carotid artery for measurement of systemic arterial blood pressure and heart rate. A sheath was placed in the right external jugular vein for introduction of a pulmonary-arterial catheter. This catheter was used for continuous measurement of pulmonary arterial blood pressure, semi-continuous cardiac output and intermittent pulmonary wedge pressure. A central venous catheter was inserted in the left external jugular vein for drug and fluid administration. All fluid and drug administrations were done by motorised syringe or drip pumps. The urinary bladder was catheterized. Respiratory gases including the fraction of nitric oxide, pressures and volumes were measured at the endotracheal tube. Respiratory and hemodynamic variables were measured by a Datex AS/3 (Helsinki, Finland) and data were collected by a computerised system (MP100 or MP150/Acknowledge 3.9.1, BIOPAC systems, Goleta, CA, USA). After surgical instrumentation, a 1 h intervention-free period followed.

12.2 Experimental Protocol

After collecting baseline data, several administration routes of PDNO (i.e. the product that comprises one of, or a mixture of, 1-(nitrosooxy)-propan-2-ol, 2-(nitrosooxy)-propan-1-ol and 1,2-bis(nitrosooxy)propane prepared as outlined above) were investigated in the same animal with stabilisation in between.

12.2.1 Nebulisation of PDNO

Pulmonary arterial pressure was increased by permissive hypercapnia (end-tidal carbon dioxide fraction of approximately 8-9%). One-part PDNO (203 mM) was dissolved in four parts of sodium bicarbonate (50 mg-1) and nebulised with an ordinary intensive care unit nebuliser for 5-20 min (n=3).

12.2.2 Inhalation of PDNO Using an E-Cigarette

A few ml of PDNO (203 mM) were applied in a commercially available electronic cigarette (eGo AIO, Joyetech). Gas from the electronic cigarette was sampled in a 50 ml syringe and injected into the inspiratory limp of the ventilator circuit. This procedure was repeated for approximately 10 times with very short interval, thus administering PDNO via inhalation (n=1).

12.2.3 Sublingual Administration of PDNO

PDNO was applied sublingually by a small compress soaked with 2 ml PDNO (1 mM-203 mM) for 10-20 min each (one or several doses in three animals). In two experiments acute pulmonary hypertension was induced by a fast injection of air (300 microl/kg) intravenously (air pulmonary embolization).

12.2.4 Dermal Application of PDNO

PDNO was applied on the skin of the abdomen by three small compresses soaked with 2 ml PDNO (203 mM). Three compresses without PDNO (control) were used for comparison. The skin was pretreated with menthone.

12.2.5 Gastrointestinal and Urinary Bladder Administration of PDNO

PDNO (2-4 ml of 1 mM, 10 mM, 100 mM and 200 mM) was injected via catheters in the urinary bladder, stomach, small and large intestine.

12.3 Results

Using pulmonary and systemic arterial pressure measurements and measurements of end-tidal concentration, it was found that PDNO administered via inhalation, nebulisation, sublingual application, dermal application, gastrointestinal application and urinary bladder administration elicited biological responses (decreases in blood pressures) via NO donation (increases in end-tidal NO concentration, not measured in all experiments (FIGS. 6 to 11). Furthermore, it was found that such administration was efficient to counteract acute pulmonary hypertension (induced either by air pulmonary embolization and hypercapnia).

The invention claimed is:

1. A method of treating a condition wherein NO has a beneficial effect, comprising administering to a patient in need thereof a therapeutically effective amount of a compound of formula (I) indirectly to the pulmonary circulation and/or the systemic circulation of the patient:

(I)

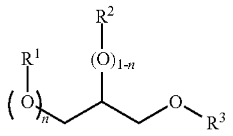

wherein $R^1$, $R^2$ and $R^3$ each independently represent H or —NO, wherein n is 0 or 1;

wherein when n is 0, $R^1$ is H; and wherein when n is 1, $R^2$ is H, provided that at least one of $R^1$ $R^2$ and $R^3$ represents —NO, wherein the condition is selected from the group consisting of: acute pulmonary vasoconstriction of different genesis, pulmonary hypertension of different genesis, preclampsia, eclampsia, erectile dysfunction, acute heart failure (with or without preserved ejection fraction (HFpEF)), coronary heart disease, myocardial infarction, ischemic heart disease, angina pectoris, instable angina, cardiac arrhythmia, acute pulmonary hypertension in cardiac surgery patients, acidosis, inflammation of the airways, cystic fibrosis, COPD, immotile cilia syndrome, inflammation of the lung, pulmonary fibrosis, acute lung injury (ALI), adult respiratory distress syndrome, acute pulmonary oedema, acute mountain sickness, asthma, bronchitis, hypoxia of different genesis, ischemic disease of different genesis, stroke, cerebral vasoconstriction, inflammation of the gastrointestinal tract, gastrointestinal dysfunction, gastrointestinal complication, IBD, Crohn's disease, ulcerous colitis, liver disease, pancreas disease, inflammation of the bladder of the urethral tract, inflammation of the urinary bladder and ureters of the urethral tract, inflammation of the skin, diabetic ulcers, diabetic neuropathy, psoriasis, wound healing, organ protection in ischemia-reperfusion conditions, organ transplantation, tissue transplantation, cell transplantation, acute kidney disease, uterus relaxation, and cervix relaxation.

2. The method of treatment according to claim 1, wherein the compound of formula (I) is present in a substantially non-aqueous composition further comprising a compound of formula (I) but wherein $R^1$, $R^2$ and $R^3$ represent H.

3. The method of treatment according to claim 1, wherein the compound of formula (I) is administered to an epithelial layer of a patient.

4. The method of treatment according to claim 1, wherein the administration is to a serous membrane, a cutaneous membrane, a synovial membrane, an uroepithelial membrane, or a mucous membrane.

5. The method of treatment according to claim 1, wherein the administration is carried out dermally, gastrointestinally, subcutaneously, intramuscularly, sublingually, intranasally, intravesically or via inhalation.

6. The method of treatment according to claim 1, wherein the administration is to an epithelial layer in the mouth, nose, eyelids, trachea, lungs, stomach, intestines, rectum, ureters, urethra or urinary bladder of the patient.

7. The method of treatment according to claim 1, wherein the condition is selected from the group consisting of pulmonary hypertension of different genesis, including primary hypertension and secondary hypertension; and acute heart failure (with or without preserved ejection fraction (HFpEF)).

8. The method of treatment according to claim 2, wherein the substantially non-aqueous composition comprises from about 0.01% to about 9% by weight of the one or more compounds of formula (I).

9. The method of treatment according to claim 2, wherein the substantially non-aqueous composition is substantially free of dissolved nitric oxide.

10. The method of treatment according to claim 2, wherein the substantially non-aqueous composition consists essentially of the one or more compounds of formula (I) and a compound of formula (I) but wherein $R^1$, $R^2$ and $R^3$ represent H.

11. The method of treatment according to claim 2, wherein the substantially non-aqueous composition is comprised in a pharmaceutical formulation, optionally comprising one or more pharmaceutically acceptable excipients.

12. The method of treatment according to claim 11, wherein the one or more pharmaceutically acceptable excipients are non-aqueous.

13. The method of treatment according to claim 1, wherein the compound of formula (I) is administered across an epithelial layer in the skin.

14. The method of treatment according to claim 1, wherein the administration is to a mucous membrane.

15. The method of treatment according to claim 14, wherein the administration is to a mucous membrane in the mouth, nose, eyelids, trachea, lungs, stomach, intestines, rectum, ureters, urethra or urinary bladder of the patient.

* * * * *